(12) United States Patent
Nishijima

(10) Patent No.: US 11,617,550 B2
(45) Date of Patent: Apr. 4, 2023

(54) X-RAY DETECTOR AND X-RAY CT APPARATUS

(71) Applicant: CANON MEDICAL SYSTEMS CORPORATION, Otawara (JP)

(72) Inventor: Akira Nishijima, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 18 days.

(21) Appl. No.: 16/732,398

(22) Filed: Jan. 2, 2020

(65) Prior Publication Data
US 2020/0214653 A1 Jul. 9, 2020

(30) Foreign Application Priority Data

Jan. 8, 2019 (JP) .............................. JP2019-000977
Nov. 26, 2019 (JP) .............................. JP2019-212859

(51) Int. Cl.
*A61B 6/00* (2006.01)
*H03M 1/12* (2006.01)
*A61B 6/03* (2006.01)

(52) U.S. Cl.
CPC ............ *A61B 6/4208* (2013.01); *A61B 6/032* (2013.01); *A61B 6/5205* (2013.01); *H03M 1/124* (2013.01)

(58) Field of Classification Search
CPC ..... A61B 6/4208; A61B 6/5205; A61B 6/032; A61B 6/54; A61B 6/5258; A61B 6/4035; A61B 6/4266; H03M 1/124; G01T 1/17
See application file for complete search history.

(56) References Cited

U.S. PATENT DOCUMENTS

| 5,677,940 | A | * | 10/1997 | Suzuki | ................... H04N 5/32 378/38 |
| 6,118,842 | A | * | 9/2000 | Arai | ........................ A61B 6/14 378/38 |
| 6,396,898 | B1 | | 5/2002 | Saito et al. | |
| 7,317,189 | B2 | | 1/2008 | Miyazaki et al. | |
| 2002/0110216 | A1 | | 8/2002 | Saito et al. | |
| 2004/0101093 | A1 | * | 5/2004 | Matsumoto | ............ A61B 6/032 378/22 |
| 2005/0253078 | A1 | | 11/2005 | Miyazaki et al. | |
| 2009/0065702 | A1 | * | 3/2009 | Kameshima | ....... H04N 5/23245 250/370.09 |
| 2017/0187928 | A1 | * | 6/2017 | Kim | ..................... H04N 5/2258 |
| 2018/0120458 | A1 | * | 5/2018 | Nakamura | ............... A61B 6/54 |
| 2019/0345819 | A1 | * | 11/2019 | Aird | ........................ G01V 5/12 |
| 2021/0102844 | A1 | * | 4/2021 | Chan | ..................... G01J 5/024 |

FOREIGN PATENT DOCUMENTS

| JP | 2001-242253 A | 9/2001 |
| JP | 2011-056325 A | 3/2011 |
| JP | 2017-086474 A | 5/2017 |

* cited by examiner

*Primary Examiner* — Marcus H Taningco
(74) *Attorney, Agent, or Firm* — Oblon, McClelland, Maier & Neustadt, L.L.P.

(57) ABSTRACT

An X-ray detector according to an embodiment includes a plurality of detection arrays, processing circuitry, and an analog-to-digital converter (ADC). The plurality of detection arrays includes a plurality of detecting elements, respectively. The processing circuitry performs the control to change the reading timings of the plurality of detecting elements between the plurality of detection arrays. The ADC processes signals from the plurality of detecting elements.

16 Claims, 17 Drawing Sheets

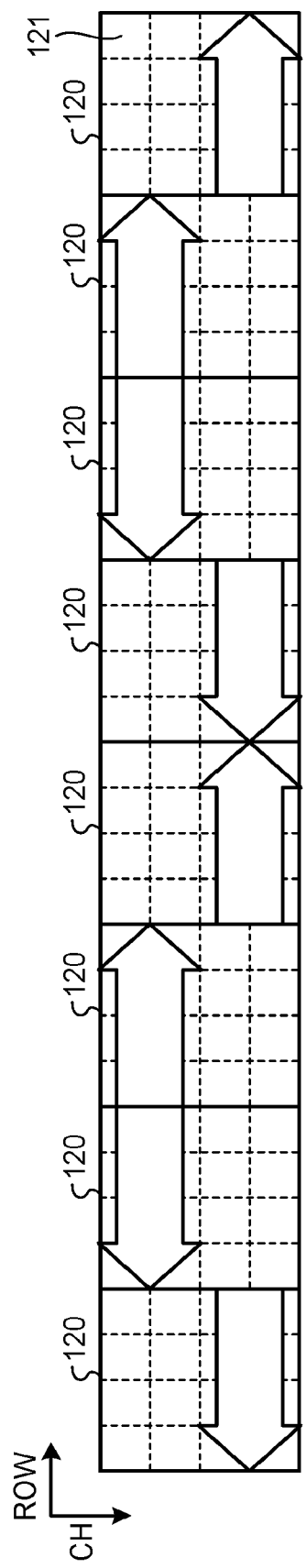

X-RAY DETECTOR AND X-RAY CT APPARATUS

CROSS-REFERENCE TO RELATED APPLICATIONS

This application is based upon and claims the benefit of priority from Japanese Patent Application No. 2019-977, filed on Jan. 8, 2019, Japanese Patent Application No. 2019-212859, filed on Nov. 26, 2019; the entire contents of which are incorporated herein by reference.

FIELD

Embodiments described herein relate generally to an X-ray detector and an X-ray CT apparatus.

BACKGROUND

Due to the recent increase in the number of rows in an X-ray detector, the data acquisition system (DAS) using a sequential acquisition method has been used for computed tomography (CT) scan. In the DAS using a sequential acquisition method, signals of X-rays detected by a plurality of detecting elements are sequentially acquired from the detecting elements in the delayed timing. For example, in the DAS using a sequential acquisition method, a single A/D converter is shared by a plurality of elements so that the A/D conversion is sequentially executed. Thus, as the single A/D converter is capable of processing signals from a plurality of detecting elements, the number of A/D converters may be lowered with respect to the number of detecting elements.

BRIEF DESCRIPTION OF THE DRAWINGS

FIG. 6A is a diagram that illustrates an example of the reading order according to the first embodiment;

DETAILED DESCRIPTION

Figure 1:
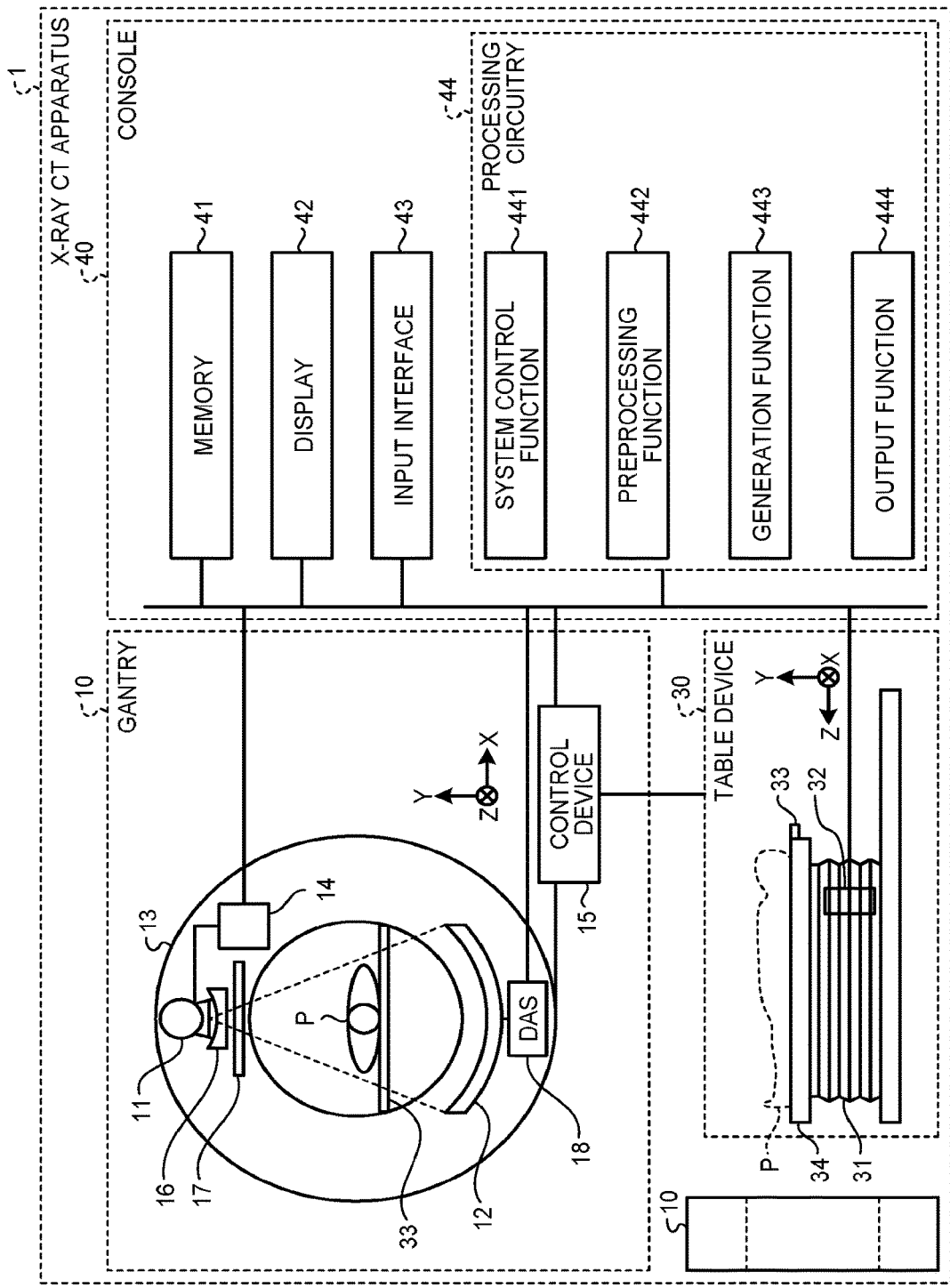
FIG. 1 is a block diagram that illustrates an example of a configuration of an X-ray CT apparatus according to a first embodiment.

According to an embodiment, an X-ray detector includes a plurality of detection arrays, processing circuitry, and an analog-to-digital converter (ADC). The plurality of detection arrays includes a plurality of detecting elements, respectively. The processing circuitry is configured to perform control to change reading timings of the plurality of detecting elements between the plurality of detection arrays. The ADC configured to process signals from the plurality of detecting elements.

With reference to the drawings, an embodiment of an X-ray detector and an X-ray CT apparatus is described below. The X-ray detector and the X-ray CT apparatus according to the subject application are not limited to the embodiments described below. In the following description, the same components are denoted by the same reference numeral, and duplicated descriptions are omitted.

First Embodiment

An X-ray CT apparatus 1 illustrated in FIG. 1 is described in a first embodiment. FIG. 1 is a block diagram that illustrates an example of the configuration of the X-ray CT apparatus 1 according to the first embodiment. As illustrated in FIG. 1, the X-ray CT apparatus 1 includes a gantry 10, a table device 30, and a console 40.

In FIG. 1, the Z-axis direction is the rotation axis of a rotary frame 13 when it is not tilted or the longitudinal direction of a tabletop 33 of the table device 30. The X-axis direction is the axis direction that is perpendicular to the Z-axis direction and that is horizontal to the floor surface. The Y-axis direction is the axis direction that is perpendicular to the Z-axis direction and that is vertical to the floor surface. FIG. 1 illustrates the gantry 10 in multiple directions for illustrative purposes and, in the illustrated case, the X-ray CT apparatus 1 includes the single gantry 10.

The gantry 10 includes an X-ray tube 11, an X-ray detector 12, the rotary frame 13, an X-ray high-voltage device 14, a control device 15, a wedge 16, a collimator 17, and a DAS 18.

The X-ray tube 11 is a vacuum tube that includes: a cathode (filament) that generates thermal electrons; and an anode (target) that generates X-rays after receiving collision of thermal electrons. The X-ray tube 11 uses a high voltage supplied from the X-ray high-voltage device 14 to emit thermal electrons from the cathode toward the anode so as to generate X-rays with which a subject P is irradiated. For example, the X-ray tube 11 includes a rotating anode X-ray tube that emits thermal electrons to the rotating anode to generate X-rays.

The X-ray detector 12 includes a plurality of detecting elements that detect X-rays. Each of the detecting elements in the X-ray detector 12 detects X-rays, which are emitted from the X-ray tube 11 and are passed through the subject P, and outputs a signal corresponding to the amount of detected X-rays to the DAS 18. The X-ray detector 12 includes for example a plurality of detecting element rows in which a plurality of detecting elements is arranged in a channel direction (a channel direction or ch direction) along one circular arc with the focal point of the X-ray tube 11 at a center. The X-ray detector 12 has a configuration such that, for example, a plurality of detecting element rows with a plurality of detecting elements arranged in the channel direction is arranged in a row direction (a slice direction or row direction).

The X-ray detector 12 is, for example, an indirect-conversion type detector that includes a grid, a scintillator array, and an optical sensor array. The scintillator array includes a plurality of scintillators. The scintillator includes a scintillator crystal that outputs light with the photon quantity corresponding to the amount of incident X-rays. The grid is provided on the surface of the scintillator array at the X-ray incident side and includes an X-ray shielding plate that absorbs scattered X-rays. The grid is sometimes called a collimator (a one-dimensional collimator or a two-dimensional collimator). The optical sensor array has a conversion function to obtain an electric signal in accordance with the amount of light from the scintillator and includes, for example, an optical sensor such as a photodiode. The X-ray detector 12 may be a direct-conversion type detector including a semiconductor element that converts incident X-rays into an electric signal.

Figure 2:
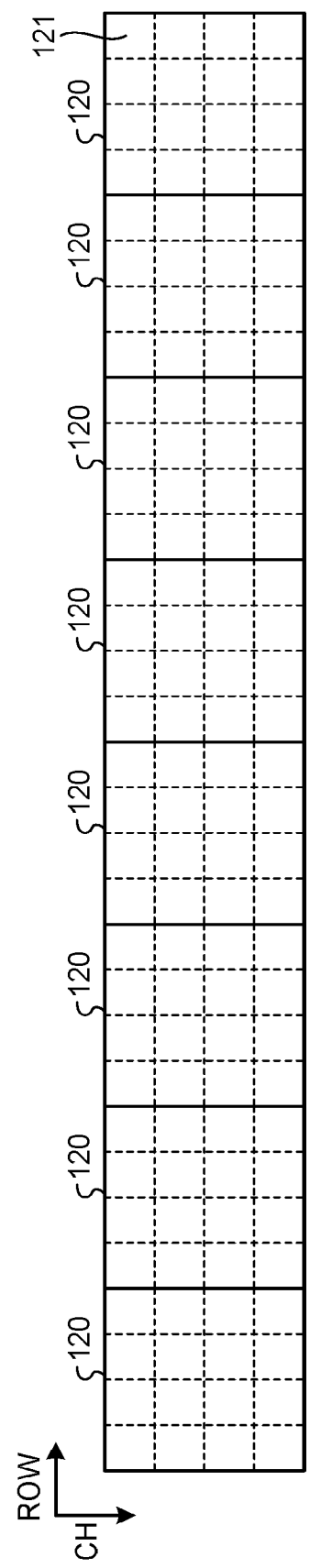
FIG. 2 is a diagram that illustrates an example of an X-ray detector according to the first embodiment.

The X-ray detector 12 according to the present embodiment has a configuration such that modules including a small number of rows are arranged in the row direction. Furthermore, the X-ray detector 12 has a configuration such that modules including a small number of channels are arranged in the channel direction. FIG. 2 is a diagram that illustrates an example of the X-ray detector 12 according to the first embodiment. FIG. 2 illustrates an example of the X-ray detector 12 including detecting elements 121 in 4 rows in the channel direction (ch in the drawing) and in 32 rows in the row direction (row in the drawing). For example, as illustrated in FIG. 2, the X-ray detector 12 has a configuration such that a module 120 includes detecting elements arranged in four rows in the channel direction and in four rows in the row direction and the modules 120 are arranged in eight rows in the row direction. Although FIG. 2 illustrates the detecting elements 121 in 4 rows in the channel direction and in 32 rows in the row direction, the X-ray detector 12 actually has a configuration such that the detecting elements 121 illustrated in FIG. 2 are arranged in multiple rows in the channel direction. That is, the X-ray detector 12 has a configuration such that each of the modules 120 include the detecting elements arranged in four rows in the channel direction and in for rows in the row direction, the modules 120 are arranged in eight rows in the row direction and in multiple rows in the channel direction, and the modules 120 are arranged like tiles. The tile arrangement of the modules 120 including the detecting elements 121 is also referred to as tiling.

With reference back to FIG. 1, the rotary frame 13 is a circular frame that supports the X-ray tube 11 and the X-ray detector 12 such that they are opposed to each other and that rotates the X-ray tube 11 and the X-ray detector 12 through the control device 15. For example, the rotary frame 13 is a cast that is made of aluminum. In addition to the X-ray tube 11 and the X-ray detector 12, the rotary frame 13 may also support the X-ray high-voltage device 14, the wedge 16, the collimator 17, the DAS 18, and the like. The rotary frame 13 may also support various components that are not illustrated in FIG. 1. Hereafter, the rotary frame 13 and a part that moves and rotates together with the rotary frame 13 in the gantry 10 are also referred to as a rotary unit.

The X-ray high-voltage device 14 includes: a high-voltage generation device that includes electric circuits such as a transformer and a rectifier and generates a high voltage to be applied to the X-ray tube 11; and an X-ray control device that controls an output voltage in accordance with X-rays emitted from the X-ray tube 11. The high-voltage generation device may be a transformer type or an inverter type. The X-ray high-voltage device 14 may be provided in the rotary frame 13 or may be provided in an undepicted fixed frame.

The control device 15 includes a processing circuit including a central processing unit (CPU), or the like, and a driving mechanism such as a motor and an actuator. The control device 15 receives an input signal from an input interface 43 to control the operation of the gantry 10 and the table device 30. For example, the control device 15 controls the rotation of the rotary frame 13, the tilt of the gantry 10, the operation of the table device 30 and the tabletop 33, and the like. With regard to the control to tilt the gantry 10, for example, the control device 15 rotates the rotary frame 13 with the axis parallel to the X-axis direction at the center on the basis of input inclination angle (tilt angle) information. The control device 15 may be provided in the gantry 10 or may be provided in the console 40.

The wedge 16 is a filter to adjust the amount of X-rays emitted from the X-ray tube 11. Specifically, the wedge 16 is a filter that allows the passage and attenuation of X-rays emitted from the X-ray tube 11 so that X-rays emitted from the X-ray tube 11 to the subject P have a predetermined distribution. For example, the wedge 16 is a wedge filter or a bow-tie filter, and it is formed by processing aluminum, or the like, to have a predetermined target angle or a predetermined thickness.

The collimator 17 is a lead plate, or the like, which narrows the irradiation range of an X-ray that has transmitted through the wedge 16, and forms a slit by combining multiple lead plates, or the like. The collimator 17 is sometimes called an X-ray limiter. Although FIG. 1 illustrates a case where the wedge 16 is provided between the X-ray tube 11 and the collimator 17, there may be a case where the collimator 17 is provided between the X-ray tube 11 and the wedge 16. In this case, the wedge 16 allows the passage and attenuation of an X-ray which is emitted from the X-ray tube 11 and whose irradiation range is limited by the collimator 17.

The DAS 18 acquires a signal of an X-ray detected by each detecting element included in the X-ray detector 12. For example, the DAS 18 includes an amplifier that performs an amplification process on an electric signal output from each detecting element and an analog-to-digital converter (A/D converter) that converts an electric signal into a digital signal to generate detection data. The DAS 18 is implemented by using, for example, a processor.

The DAS 18 sequentially acquires the signal of an X-ray from each detecting element group in the X-ray detector 12. That is, the DAS 18 is a DAS using a sequential acquisition method. For example, the DAS 18 is connected to each detecting element in a detecting element group via a switch to sequentially read the electric charge integrated by each detecting element while switching the detecting element to be connected.

Data generated by the DAS 18 is transmitted from a transmitter including a light emitting diode (LED) provided in the rotary frame 13 to a receiver including a photodiode provided in a non-rotary section (e.g., a fixed frame, which is not illustrated in FIG. 1) of the gantry 10 through optical communications and is transferred to the console 40. Here, the non-rotary section is, for example, a fixed frame that rotatably supports the rotary frame 13. As the method for transmitting data from the rotary frame 13 to the non-rotary section in the gantry 10, any non-contact type data transmission method or any contact-type data transmission method may be used in addition to optical communications.

The table device 30 is a device on which the subject P, which is the target to be captured, is placed and moved, and includes a base 31, a table driving device 32, the tabletop 33, and a support frame 34. The base 31 is a chassis that movably supports the support frame 34 in a vertical direction. The table driving device 32 is a driving mechanism that moves the tabletop 33 on which the subject P is placed in the long axis direction of the tabletop 33, and includes a motor, an actuator, and the like. The tabletop 33 provided on the top surface of the support frame 34 is a plate on which the subject P is placed. The table driving device 32 may move the support frame 34 as well as the tabletop 33 in the long axis direction of the tabletop 33.

The console 40 includes a memory 41, a display 42, an input interface 43, and processing circuitry 44. Although the console 40 is separate from the gantry 10 in the description, the gantry 10 may include the console 40 or a part of the components of the console 40.

The memory 41 is implemented by using, for example, a semiconductor memory device such as a random access memory (RAM) or a flash memory, a hard disk, or an optical disk. For example, the memory 41 stores projection data or reconstruction image data. For example, the memory 41 stores a program for a circuit included in the X-ray CT apparatus 1 to perform its function. The memory 41 may be implemented by using a server group (cloud) connected to the X-ray CT apparatus 1 via a network.

The display 42 presents various types of information. For example, the display 42 presents various images generated by the processing circuitry 44 and displays the graphical user interface (GUI) for receiving various operations from an operator. For example, the display 42 is a liquid crystal display or a cathode ray tube (CRT) display. The display 42 may be a desktop type or may be configured by using a tablet terminal, or the like, enabling wireless communications with the main body of the console 40.

The input interface 43 receives various input operations from an operator, converts the received input operation into an electric signal, and outputs it to the processing circuitry 44. For example, the input interface 43 receives, from an operator, an input operation for the acquisition condition (capturing condition) to acquire projection data. The capturing condition is described in detail later. For example, the input interface 43 receives, from an operator, a reconstruction condition to reconstruct CT image data or an input operation for the image processing condition, or the like, to generate a post-processing image from CT image data.

For example, the input interface 43 is implemented by using, for example, a mouse, a keyboard, a trackball, a switch, a button, a joystick, a touch-pad on which an input operation is performed due to the contact with the operation surface, a touch screen in which a display screen and a touch-pad are integrated, a non-contact input circuit using an optical sensor, or a sound input circuit. The input interface 43 may be provided in the gantry 10. The input interface 43 may be configured by using a tablet terminal, or the like, enabling wireless communications with the main body of the console 40. The input interface 43 is not limited to the one including a physical operating component such as a mouse or a keyboard. Examples of the input interface 43 include an electric-signal processing circuit that receives an electric signal corresponding to an operation input from an external input device, which is separate from the console 40, and outputs the electric signal to the processing circuitry 44.

The processing circuitry 44 controls the overall operation of the X-ray CT apparatus 1. The processing circuitry 44 is not always included in the console 40. For example, the processing circuitry 44 may be included in an integration server that collectively performs processing on detection data acquired by multiple medical image diagnostic apparatuses. For example, the processing circuitry 44 performs a system control function 441, a preprocessing function 442, a generation function 443, and an output function 444.

The system control function 441 controls various processes of the X-ray CT apparatus 1 based on an input operation received from the operator via the input interface 43. For example, the system control function 441 controls the table driving device 32, the collimator 17, the control device 15, the X-ray high voltage device 14, or the like, in the X-ray CT apparatus 1 so as to perform the position-fixed scan or the primary scan.

The preprocessing function 442 performs logarithmic conversion processing or correction processing such as offset correction, sensitivity correction, or beam hardening correction on detection data transmitted from the DAS 18 to generate projection data. The preprocessing function 442 stores the generated projection data in the memory 41. Data (detection data) before preprocessing and data after preprocessing are sometimes collectively referred to as projection data.

The generation function 443 generates various images from projection data stored in the memory 41 and stores the generated image in the memory 41. For example, the generation function 443 reconstructs projection data by using various reconstruction methods (e.g., a back projection method such as a filtered back projection (FBP) or a successive approximation method) to reconstruct CT image data and stores the reconstructed CT image data in the memory 41. The generation function 443 performs various types of image processing to generate a CT image such as an MPR image from CT image data and stores the generated CT image in the memory 41.

The output function 444 outputs a CT image, CT image data, and the like. For example, the output function 444 causes the display 42 to present a CT image. Furthermore, for example, the output function 444 outputs CT image data to an external device (e.g., a server device that stores image data) connected to the X-ray CT apparatus 1 via a network.

In the X-ray CT apparatus 1 illustrated in FIG. 1, the memory 41 stores each processing function in the form of program executable by a computer. The processing circuitry 44 is a processor that reads and executes a program from the memory 41 to perform the function corresponding to the program. In other words, after having read each program, the processing circuitry 44 provides the function corresponding to the read program.

In the case illustrated in FIG. 1, each processing function, i.e., the system control function 441, the preprocessing function 442, the generation function 443, and the output function 444, is performed by using the single processing circuitry 44; however, this is not a limitation on the embodiment. For example, the processing circuitry 44 may be configured by combining multiple independent processors so that each processor executes each program to perform each processing function. Each processing function provided by the processing circuitry 44 may be performed by being separated or combined in one or more processing circuitries as appropriate.

The overall configuration of the X-ray CT apparatus 1 according to the present embodiment is described above. With the above configuration, the X-ray CT apparatus 1 according to the present embodiment may execute the sequential acquisition appropriately with the X-ray detector using modules including a plurality of detecting elements. Specifically, the X-ray CT apparatus 1 may execute the sequential acquisition appropriately with the X-ray detector in which modules including a plurality of detecting elements are arranged in at least one of the row direction and the channel direction. More specifically, the reading timings of the modules are adjusted in accordance with the reading timing of each detecting element so that the sequential acquisition may be appropriately executed.

First, a sequential acquisition method is described. For example, in the sequential acquisition method, an ADC is provided for each detecting element group including a plurality of (e.g., 32 in FIG. 2) detecting elements arranged in the row direction of the X-ray detector 12. That is, the ADCs are provided corresponding to the number of channels. The DAS 18 is connected to each detecting element group via a switch so as to sequentially acquire signals of X-rays detected by the detecting element group while the X-ray tube 11 generates X-rays.

For example, the DAS 18 establishes the connection with a first detecting element in a detecting element group to read the electric charge integrated by the first detecting element as the signal of an X-ray. Then, the DAS 18 terminates the connection with the first detecting element and establishes the connection with a second detecting element adjacent to the first detecting element to read the electric charge integrated by the second detecting element as the signal of an X-ray. When the connection with the DAS 18 is terminated, each detecting element starts to integrate an electric charge. In the same manner, the DAS 18 performs the control on each detecting element in the detecting element group so as to sequentially read the electric charge integrated by each detecting element as the signal of an X-ray.

The DAS 18 performs the above-described control for each view to acquire the detection data on the view. That is, the DAS 18 sequentially acquires signals corresponding to the number of elements from the detecting element group with regard to a single view. Similarly, the DAS 18 sequentially acquires signals corresponding to the number of elements with regard to the subsequent view.

As described above, in the sequential acquisition method, signals are sequentially acquired from a plurality of detecting elements arranged in the row direction; however, when the detecting elements are tiled like the X-ray detector 12 according to the present embodiment, there is a gap in the reading timing between two adjacent detecting elements in modules, which may result in the occurrence of an artifact.

In the case described below, for example, the X-ray detector 12 tiled as illustrated in FIG. 2 executes the above-described sequential acquisition. For example, when the X-ray detector 12 illustrated in FIG. 2 executes the sequential acquisition in the row direction, an ADC is provided for each of the modules 120 so that the sequential acquisition is executed for each module in the row direction.

For example, when the sequential acquisition is executed in each of the modules 120 of FIG. 2 from the detecting element 121 on the extreme right to the detecting element 121 on the extreme left in the row direction that is a horizontal direction, there is a large gap in the reading timing between the adjacent detecting elements 121 in the adjacent modules 120. For example, the extreme-right detecting element 121 in the extreme-left module 120 of FIG. 2 is read at the start timing of the sequential acquisition, while the extreme-left detecting element 121 in the second module 120 from the left of FIG. 2 is read at the timing of the third acquisition after the start of the sequential acquisition.

That is, when the sequential acquisition simultaneously starts in each of the modules 120, the reading timing of the extreme-right detecting element 121 comes first, and the reading timing of the extreme-left detecting element 121 comes last among the four detecting elements of the module 120 in the row direction. Therefore, although the extreme-right detecting element 121 and the extreme-left detecting element 121 are adjacent to each other, there is a large gap in the reading timing, which may result in an artifact. As there is no large gap in the reading timing between the detecting elements 121 included in the same module 120 during the sequential acquisition, no recognizable artifact occurs.

As described above, in the X-ray detector 12 where the modules each including a plurality of detecting elements are arranged in the row direction, the typical sequential acquisition may cause an artifact. Therefore, the X-ray CT apparatus 1 according to the first embodiment adjusts the reading timings relative to the modules in accordance with the reading timing of each detecting element so as to execute the sequential acquisition appropriately.

Figure 3:
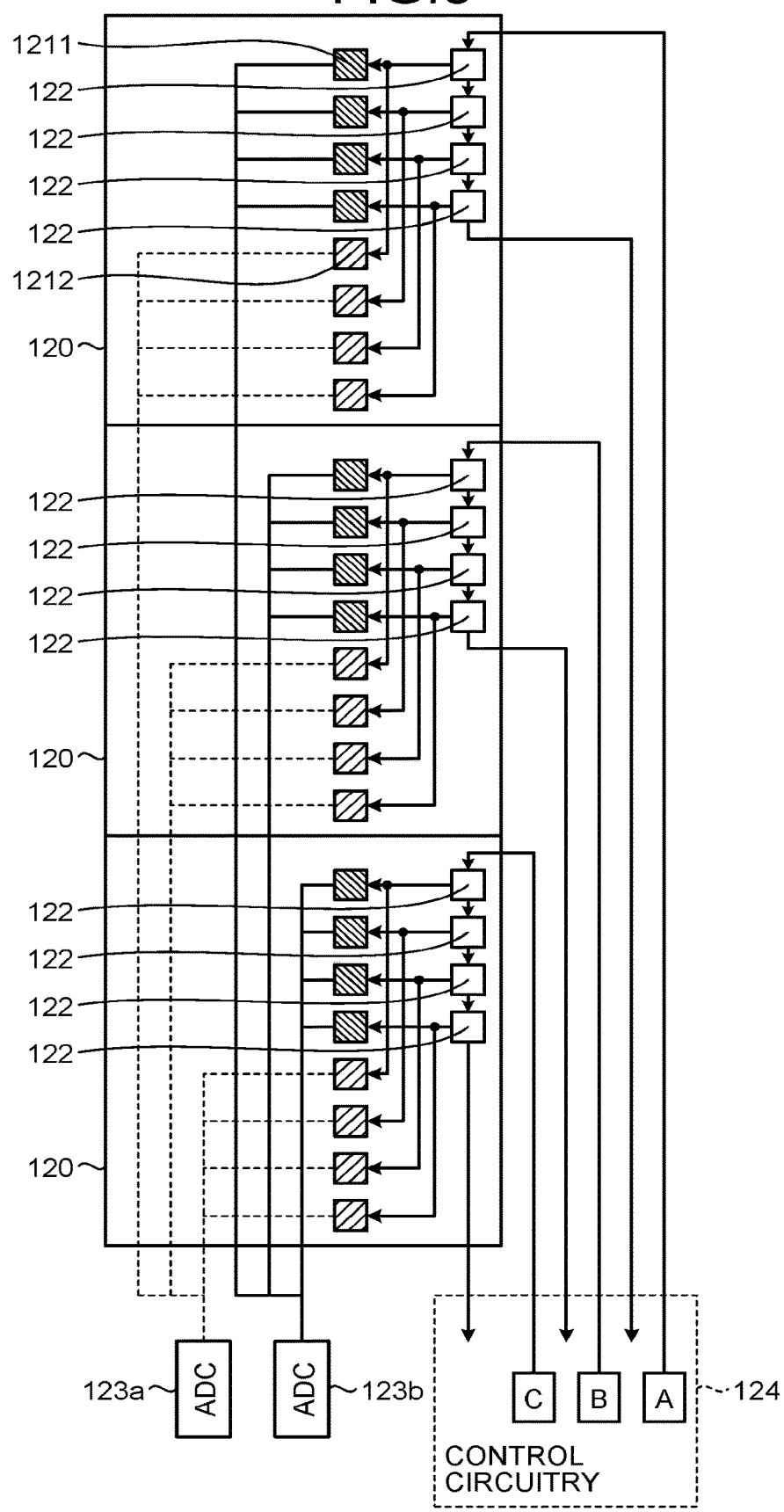
FIG. 3 is a diagram that illustrates an example of a circuitry configuration of the X-ray detector according to the first embodiment.

FIG. 3 is a diagram that illustrates an example of the circuitry configuration of the X-ray detector 12 according to the first embodiment. FIG. 3 illustrates the circuitry configuration of the three modules 120 arranged in the row direction; however, in actuality, the eight modules 120 are arranged in the row direction, as illustrated in FIG. 2.

For example, as illustrated in FIG. 3, the X-ray detector 12 includes the modules 120, an ADC 123a, an ADC 123b, and a control circuitry 124. The module 120 is an example of a detection array. The ADC 123a and the ADC 123b are examples of a processing unit. The control circuitry 124 is an example of a control unit.

Each of the modules 120 includes the detecting elements 121. For example, each of the modules 120 includes the four detecting elements 1211 and the four detecting elements 1212. The detecting elements 1211 and the detecting elements 1212 in the module 120 illustrated in FIG. 3 represent four detecting elements arranged in the row direction. That is, although the four detecting elements 1211 and the four detecting elements 1212 are arranged in one row in FIG. 3, the four detecting elements 1211 and the four detecting elements 1212 are arranged in the channel direction in actuality.

For example, the four detecting elements 1211 correspond to the four detecting elements in the top channel of the module in FIG. 2 in the row direction that is a horizontal direction. The four detecting elements 1212 correspond to the four detecting elements in the second channel of the module in FIG. 2 from the top in the row direction that is a horizontal direction.

The detecting element 1211 is connected to a switch 122 and the ADC 123b. The detecting element 1211 outputs an electric signal to the ADC 123b in response to a start pulse signal (SP signal) input from the control circuitry 124 to the switch 122. The detecting element 1212 is connected to the switch 122 and the ADC 123a. The detecting element 1212 outputs an electric signal to the ADC 123a in response to an SP signal input from the control circuitry 124 to the switch 122. FIG. 3 illustrates that each of the modules 120 includes detecting element groups in two rows in the channel direction; however, in actuality, detecting element groups in two more rows in the channel direction are included, and each of the detecting element groups is connected to the switch and the ADC. The control content that is the same as that described below is performed on each of the detecting element groups.

The switch 122 is, for example, a shift register, and is provided in each of the modules 120 to receive an SP signal from the control circuitry 124 and selectively establish or terminate the connection with each detecting element. Each of the modules 120 according to the present embodiment includes a port to receive an SP signal from the control circuitry 124. That is, each of the modules 120 receives a unique SP signal from the control circuitry 124.

The ADC 123a receives electric signals sequentially output from the detecting elements 1212 included in each of the modules 120 and converts them into digital signals. The ADC 123b converts electric signals sequentially output from the detecting elements 1211 included in each of the modules 120 into digital signals. Although not illustrated, before the ADC 123a and the ADC 123b, an amplifier is provided to perform an amplification process on an electric signal output from a detecting element. There may be a case where the ADC 123a and the ADC 123b are installed on a board provided after the detecting element 121 or installed on the DAS 18.

The control circuitry 124 performs the control to change the reading timings of the detecting elements in the modules 120. Specifically, the control circuitry 124 is installed on the board provided after the detecting element 121 or the DAS 18 to delay the reading timings of the detecting elements in the modules 120. More specifically, the control circuitry 124 transmits a unique SP signal to each of the modules to adjust the reading timing of each module. For example, the control circuitry 124 transmits an SP signal "A" to the switches 122 in the upper module 120 of FIG. 3 to sequentially acquire electric signals from the four detecting elements 1211 and the four detecting elements 1212. For example, the switches 122 transmit the SP signal by one clock in the direction of the arrows between the switches 122 to switch the connection by one clock so as to execute the sequential acquisition in the reading timing delayed by one clock.

Similarly, the control circuitry 124 transmits an SP signal "B" to the switches 122 in the middle module 120 of FIG. 3 to sequentially acquire electric signals from the four detecting elements 1211 and the four detecting elements 1212 in the middle module 120. The SP signal "B" is a signal controlled such that the reading in the middle module 120 is started in the timing delayed by one clock after the last reading based on the SP signal "A". Thus, the reading of the detecting element 1211 and the detecting element 1212 in the middle module 120, which are adjacent to the detecting element 1211 and the detecting element 1212 in the upper module 120, is started one clock after the end of the reading in the upper module 120.

Similarly, the control circuitry 124 transmits an SP signal "C" to the switches 122 in the lower module 120 of FIG. 3 to sequentially acquire electric signals from the four detecting elements 1211 and the four detecting elements 1212 in the lower module 120. The SP signal "C" is a signal controlled such that the reading in the lower module 120 is started in the timing delayed by one clock after the last reading based on the SP signal "B". Thus, the reading of the detecting element 1211 and the detecting element 1212 in the lower module 120, which are adjacent to the detecting element 1211 and the detecting element 1212 in the middle module 120, is started one clock after the end of the reading in the middle module 120.

As described above, the X-ray detector 12 according to the first embodiment controls the reading timing of each module based on an SP signal so as to prevent a gap in the reading timing between the modules and enable the sequential acquisition appropriately.

The control circuitry 124 applies a delay in accordance with the reading order of the modules and the reading order of the detecting elements included in the modules. That is, the sequential acquisition may be executed in various reading orders in a case where the reading timing is controlled for each module based on an SP signal so as to prevent a gap in the reading timing between the modules.

Variations of the reading order are described below with reference to FIGS. 4A to 7B. FIGS. 4A, 5A, 6A, and 7A are diagrams that illustrate examples of the reading order according to the first embodiment. FIGS. 4B, 5B, 6B, and 7B are diagrams that illustrate examples of the circuitry configuration of an X-ray detector according to the first embodiment. FIG. 4B illustrates the circuitry configuration to achieve the reading order illustrated in FIG. 4A. FIG. 5B illustrates the circuitry configuration to achieve the reading order illustrated in FIG. 5A. FIG. 6B illustrates the circuitry configuration to achieve the reading order illustrated in FIG. 6A. FIG. 7B illustrates the circuitry configuration to achieve the reading order illustrated in FIG. 7A. FIGS. 4B, 5B, 6B, and 7B illustrate part of the X-ray detector 12 in the same manner as FIG. 3.

Figure 4A:
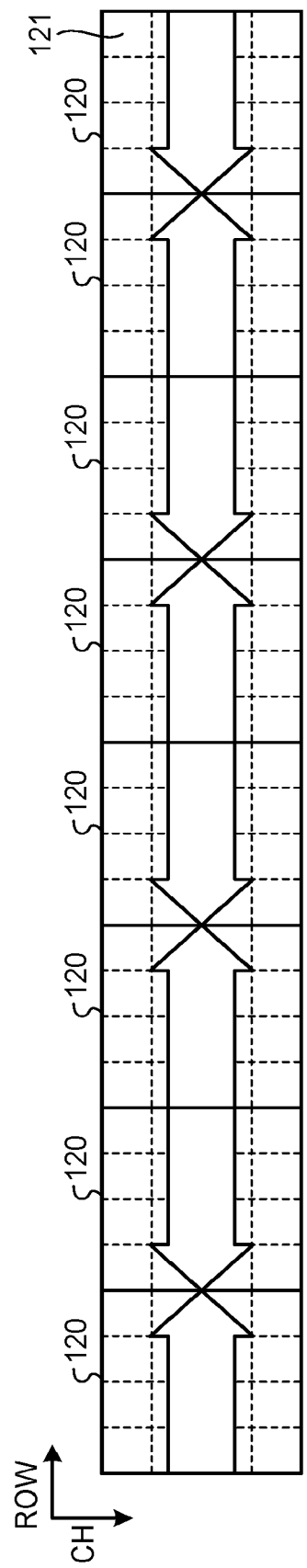
FIG. 4A is a diagram that illustrates an example of a reading order according to the first embodiment.
Figure 4B:
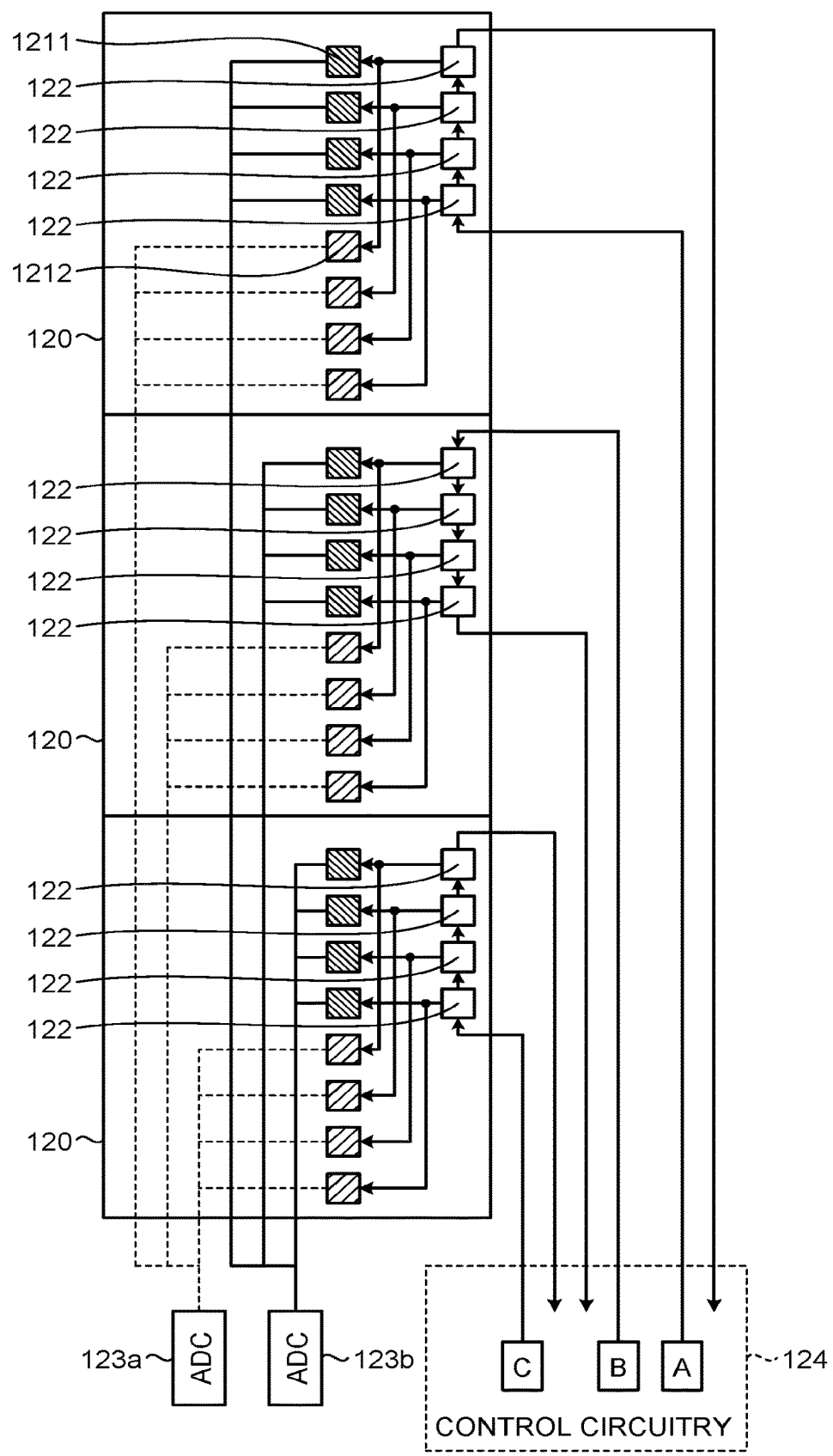
FIG. 4B is a diagram that illustrates an example of the circuitry configuration of the X-ray detector according to the first embodiment.

For example, in the X-ray detector 12 according to the first embodiment, the reading may be executed in the adjacent modules 120 in the opposite directions, as illustrated in FIG. 4A. In FIG. 4A, in a case where the row direction is a horizontal direction, the arrow at the same level indicates the start of reading in the same timing. That is, FIG. 4A indicates that, as all the arrows are at the same level, the reading at the start point is simultaneously started in each of the modules 120 in the reading order in the direction from the start point to the end point of the arrow.

In the case of the reading order illustrated in FIG. 4A, the X-ray detector 12 includes the circuitry configuration illustrated in for example FIG. 4B. FIG. 4B illustrates the circuitry configuration of the three modules from the left in the row direction that is a horizontal direction in the X-ray detector 12 of FIG. 4A. Specifically, the lower end of the module 120 in FIG. 4A corresponds to the lower end of the module 120 in FIG. 4B. For example, in the X-ray detector 12 as illustrated in FIG. 4B, the input direction of SP signals in the upper module 120 and the lower module 120 is different from that in FIG. 3. That is, in the X-ray detector 12 illustrated in FIG. 4B, the SP signal "A" and the SP signal "C" are input to the switches 122 such that the reading is started at the detecting element on the reading start side indicated by the start point of the arrow in FIG. 4A.

The control circuitry 124 illustrated in FIG. 4B transmits the SP signals "A", "B", and "C" so as to simultaneously start the reading in all the modules 120. That is, according to the reading order illustrated in FIG. 4A, the reading is executed in the adjacent modules 120 in the opposite directions, and therefore there is no large gap in the reading timing at the boundary between the modules.

Figure 5A:
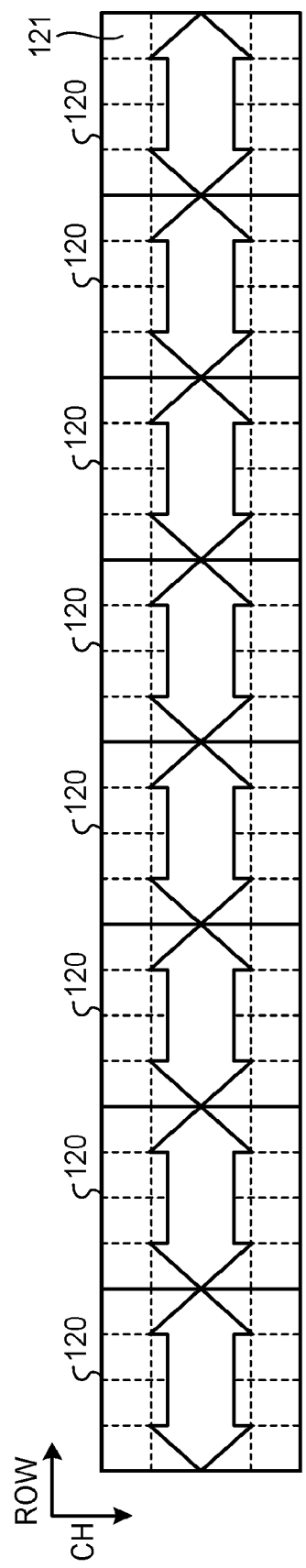
FIG. 5A is a diagram that illustrates an example of the reading order according to the first embodiment.
Figure 5B:
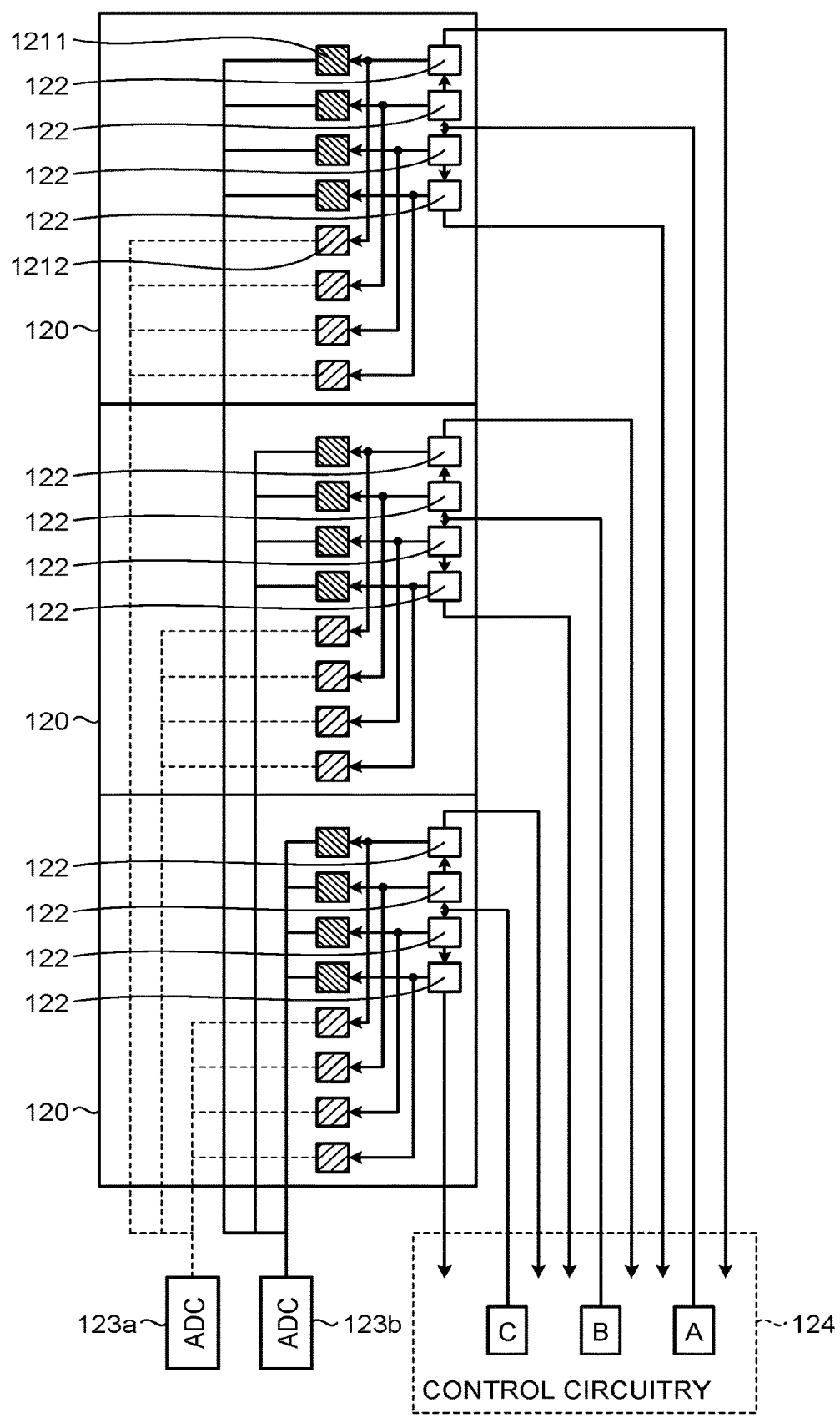
FIG. 5B is a diagram that illustrates an example of the circuitry configuration of the X-ray detector according to the first embodiment.
Figure 6B:
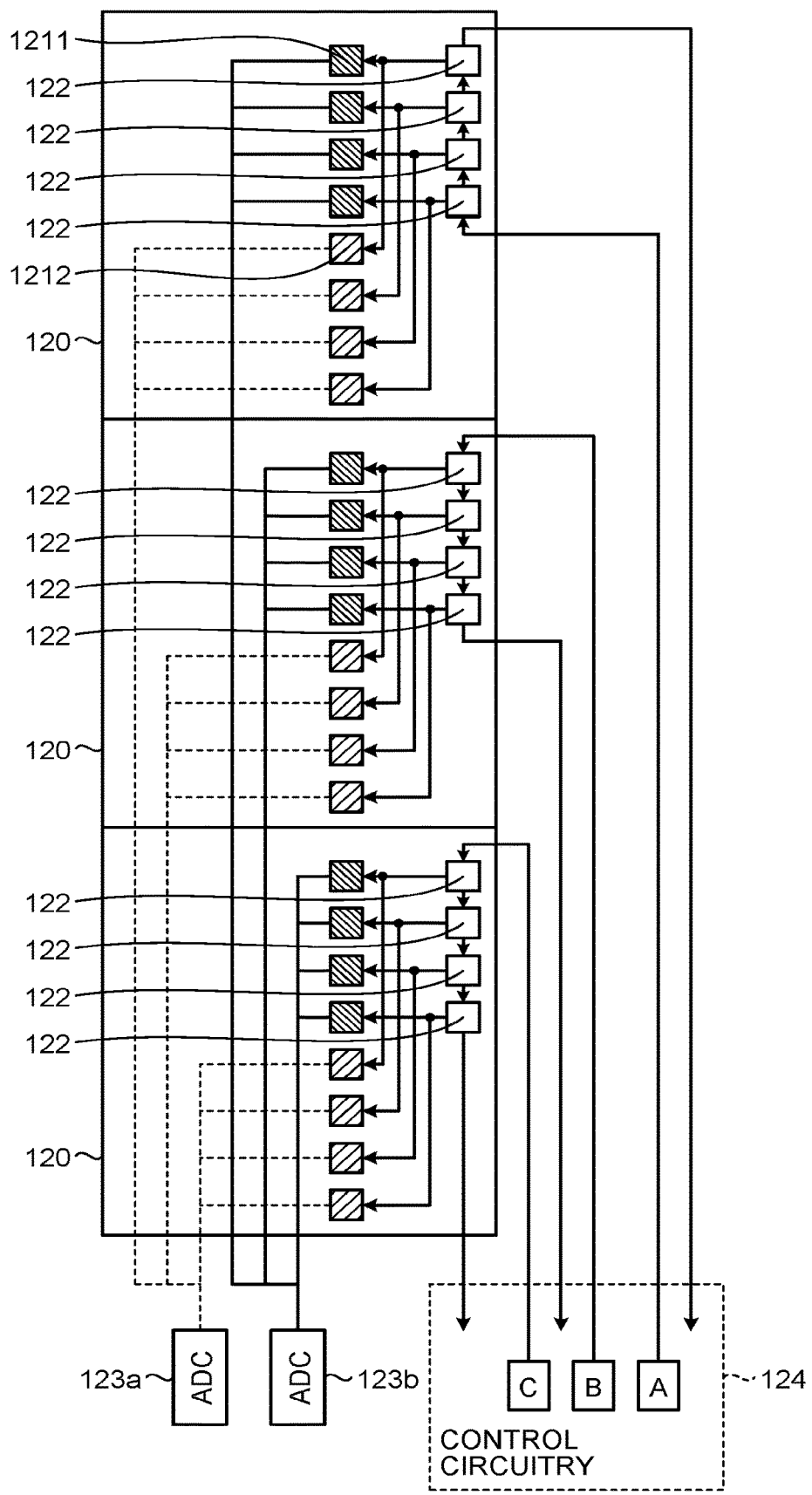
FIG. 6B is a diagram that illustrates an example of the circuitry configuration of the X-ray detector according to the first embodiment.

For example, in the X-ray detector 12 according to the first embodiment, the reading may be executed in each of the modules 120, starting from the detecting elements corresponding to the center to the outer side, as illustrated in FIG. 5A. In FIG. 5A, all the double-headed arrows at the same level indicate that the reading is simultaneously started at the center in each of the modules 120 in the reading order in the direction from the center of the double-headed arrow to the outer side.

In the case of the reading order illustrated in FIG. 5A, the X-ray detector 12 includes the circuitry configuration illustrated in for example FIG. 5B. FIG. 5B illustrates the circuitry configuration of the three modules from the left in the row direction that is a horizontal direction in the X-ray detector 12 of FIG. 5A. Specifically, the lower end of the module 120 in FIG. 5A corresponds to the lower end of the module 120 in FIG. 5B. For example, as illustrated in FIG. 5B, the X-ray detector 12 is different from that in FIG. 3 in that, in each of the modules 120, an SP signal is input from the center to the right and left sides. Specifically, in the X-ray detector 12 illustrated in FIG. 5B, the SP signals "A", "B", and "C" are input to the switches 122 such that the reading is started at the detecting elements corresponding to the reading start position indicated by the center of the double-headed arrow in FIG. 5A.

In the X-ray detector 12 illustrated in FIG. 5B, the control is performed such that, when the reading is executed, starting from the detecting element corresponding to the reading start position in each of the modules 120 to the right and left sides, the reading order of the detecting elements on the right and left are not overlapped. For example, the X-ray detector 12 performs the control such that clock signals are alternately input from the center of the four detecting elements 1211 to the detecting elements 1211 on the right and left so that the electric signals from the detecting elements 1211 on the right and left are alternately read.

The control circuitry 124 illustrated in FIG. 5B transmits the SP signals "A", "B", and "C" to simultaneously start the reading in all the modules 120. That is, in the reading order illustrated in FIG. 5A, the reading is executed, starting at the detecting elements corresponding to the center to the outer side, whereby there is no large gap in the reading timing at the boundary between the modules.

For example, in the X-ray detector 12 according to the first embodiment, as illustrated in FIG. 6A, the reading in different directions and the reading in the same direction may be combined for the adjacent modules 120. For example, as illustrated in FIG. 6A, in the X-ray detector where the eight modules are arranged in the row direction, the reading order may be achieved such that the reading direction is reversed at every two adjacent modules 120.

In FIG. 6A, the arrows at different levels indicate different reading start timings. Furthermore, in FIG. 6A, the arrows at the same level indicate the same reading start timing. For example, in FIG. 6A, as the arrows in the same direction in adjacent modules are at different levels, the reading is started at the start point of the arrow in different timing. Specifically, the reading is started at the start point of the arrow at a higher position and, after the reading at the end point of the arrow at the higher position, the reading is started at the start point of the arrow at a lower position. For example, in FIG. 6A, as the arrows in different directions in adjacent modules are at the same level, the reading is started at the start point of the arrow in the same timing.

In the case of the reading order illustrated in FIG. 6A, the X-ray detector 12 includes the circuitry configuration illustrated in for example FIG. 6B. FIG. 6B illustrates the circuitry configuration of the three modules from the left in the row direction that is a horizontal direction in the X-ray detector 12 of FIG. 6A. Specifically, the lower end of the module 120 in FIG. 6A corresponds to the lower end of the module 120 in FIG. 6B. For example, in the X-ray detector 12 as illustrated in FIG. 6B, the input direction of SP signals in the upper module 120 is different from that in FIG. 3. That is, in the X-ray detector 12 illustrated in FIG. 6B, the SP signal "A" is input to the switch 122 such that the reading is started at the detecting element on the reading start side indicated by the start point of the arrow in FIG. 6A.

The control circuitry 124 illustrated in FIG. 6B transmits the SP signal so as to cause the adjacent modules 120, which start the reading in different directions, to simultaneously start the reading. For example, the control circuitry 124 transmits the SP signals "A" and "B" to the top and the middle modules 120, respectively, so as to simultaneously start the reading. Conversely, the control circuitry 124 transmits the SP signal so as to cause the adjacent modules 120, which start the reading in the same direction, to start the reading in different timings. For example, the control circuitry 124 transmits the SP signal "C" to the lower module 120 so as to start the reading at the timing delayed by one clock after the middle module 120 has finished the reading.

That is, according to the reading order illustrated in FIG. 6A, the reading is started in the same timing in the adjacent modules 120 when the reading is executed in the opposite directions, and the reading timing is delayed when the reading is executed in the same direction; thus, there is no large gap in the reading timing at the boundary between the modules.

Figure 7A:
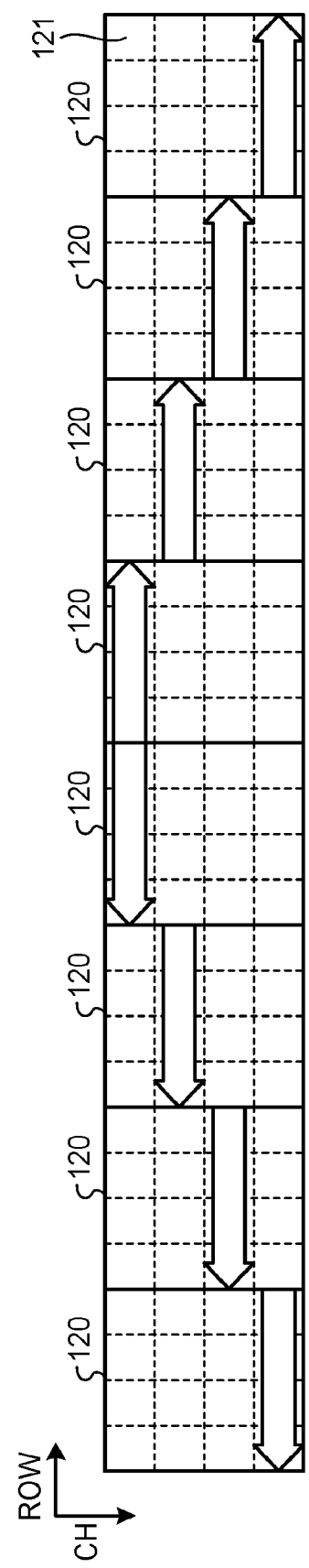
FIG. 7A is a diagram that illustrates an example of the reading order according to the first embodiment.
Figure 7B:
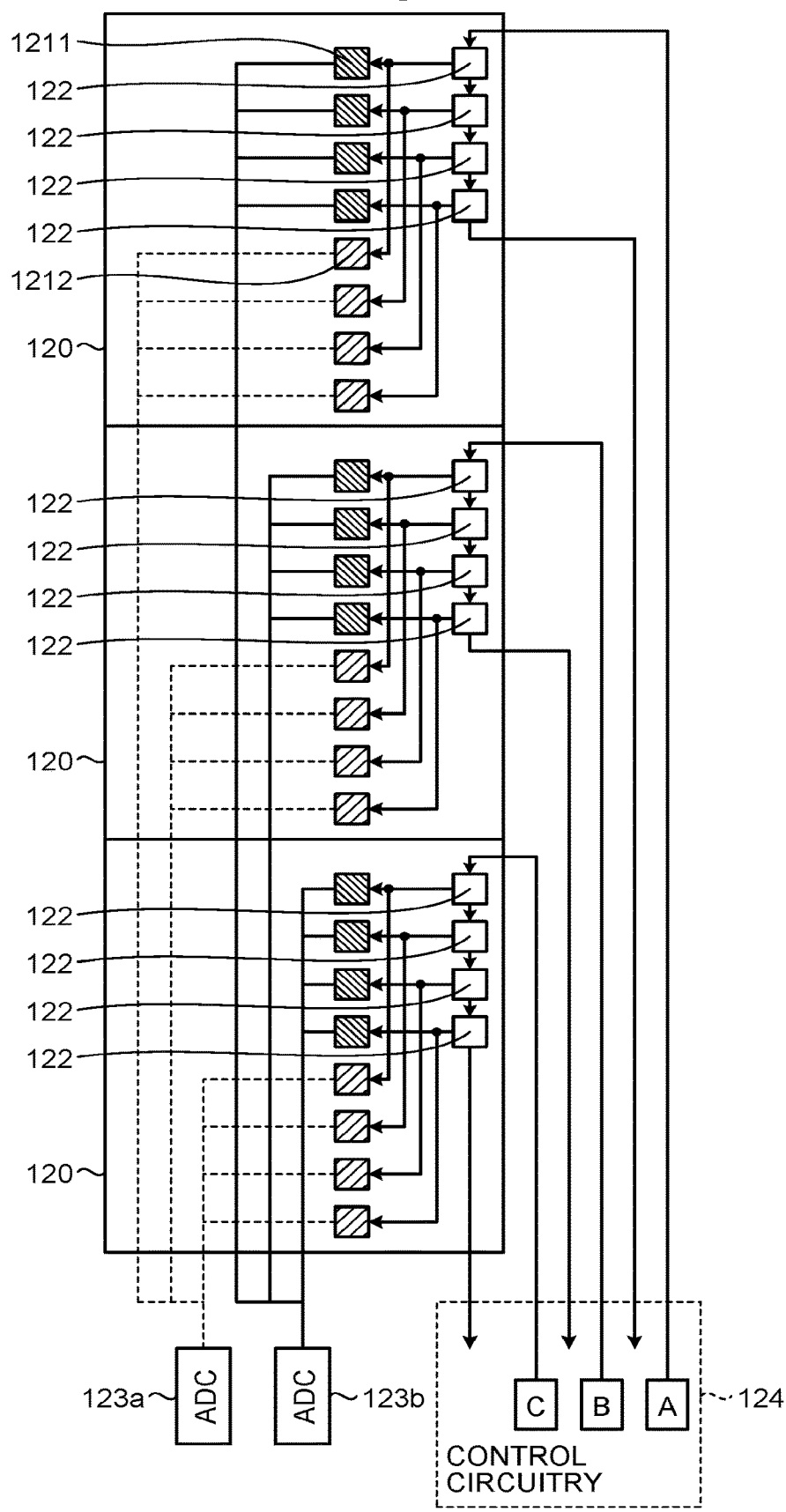
FIG. 7B is a diagram that illustrates an example of the circuitry configuration of the X-ray detector according to the first embodiment.

In a case where the reading in different directions and the reading in the same direction are combined in the adjacent modules 120, for example, the X-ray detector 12 according to the first embodiment may execute the reading illustrated in FIG. 7A. For example, as illustrated in FIG. 7A, in the X-ray detector where the eight modules are arranged in the row direction, the reading order may be achieved such that the reading direction is reversed at the boundary between module groups including the successive four modules 120.

In FIG. 7A, the arrows at different levels indicate different reading start timings. Furthermore, in FIG. 7A, the arrows at the same level indicate the same reading start timing. For example, in FIG. 7A, as the arrows in the same direction in modules are at different levels, the reading is started at the start point of the arrow in different timing. Specifically, the reading is started at the start point of the arrow at a higher position and, after the reading at the end point of the arrow at the higher position, the reading is started at the start point of the arrow at a lower position. For example, in FIG. 7A, as the arrows are at the same level in modules, the reading is started at the start point of the arrow in the same timing.

In the case of the reading order illustrated in FIG. 7A, the X-ray detector 12 includes the circuitry configuration illustrated in for example FIG. 7B. FIG. 7B illustrates the circuitry configuration of the three modules from the left in the row direction that is a horizontal direction in the X-ray detector 12 of FIG. 7A. Specifically, the lower end of the module 120 in FIG. 7A corresponds to the lower end of the module 120 in FIG. 7B. For example, in the X-ray detector 12 as illustrated in FIG. 7B, the reading order illustrated in FIG. 7A may be achieved with the same circuitry configuration as that in FIG. 3.

That is, in the case of the reading order illustrated in FIG. 7A, the reading start timing is delayed with regard to the modules in which the reading is executed in the same direction, and the same reading timing is set with regard to the adjacent modules in which the reading is executed in different directions. Thus, there is no large gap in the reading timing at the boundary between the modules.

As described above, according to the first embodiment, the modules 120 include the detecting elements 121. The control circuitry 124 delays the reading timings of the detecting elements 121 between the modules 120. The ADC processes signals from the detecting elements 121. Thus, the X-ray CT apparatus 1 according to the first embodiment may prevent the occurrence of a large gap in the reading timing at the boundary between the modules 120 and may appropriately execute the sequential acquisition in the X-ray detector 12 in which the modules 120 including the detecting elements 121 are arranged in the row direction. As a result, the X-ray CT apparatus 1 makes it possible to configure the X-ray detector 12 by tiling without degrading the performance of the sequential acquisition and achieve the low cost and the wide coverage of the detector.

Second Embodiment

In the case described according to the above first embodiment, the reading start timing is adjusted for each of the modules 120. In the case described according to a second embodiment, the modules 120 are connected with a control line for controlling the reading timing so that the sequential acquisition is appropriately executed. Specifically, in the case described, the modules 120 are connected in a daisy chain in the X-ray detector 12 according to the second embodiment.

Figure 8:
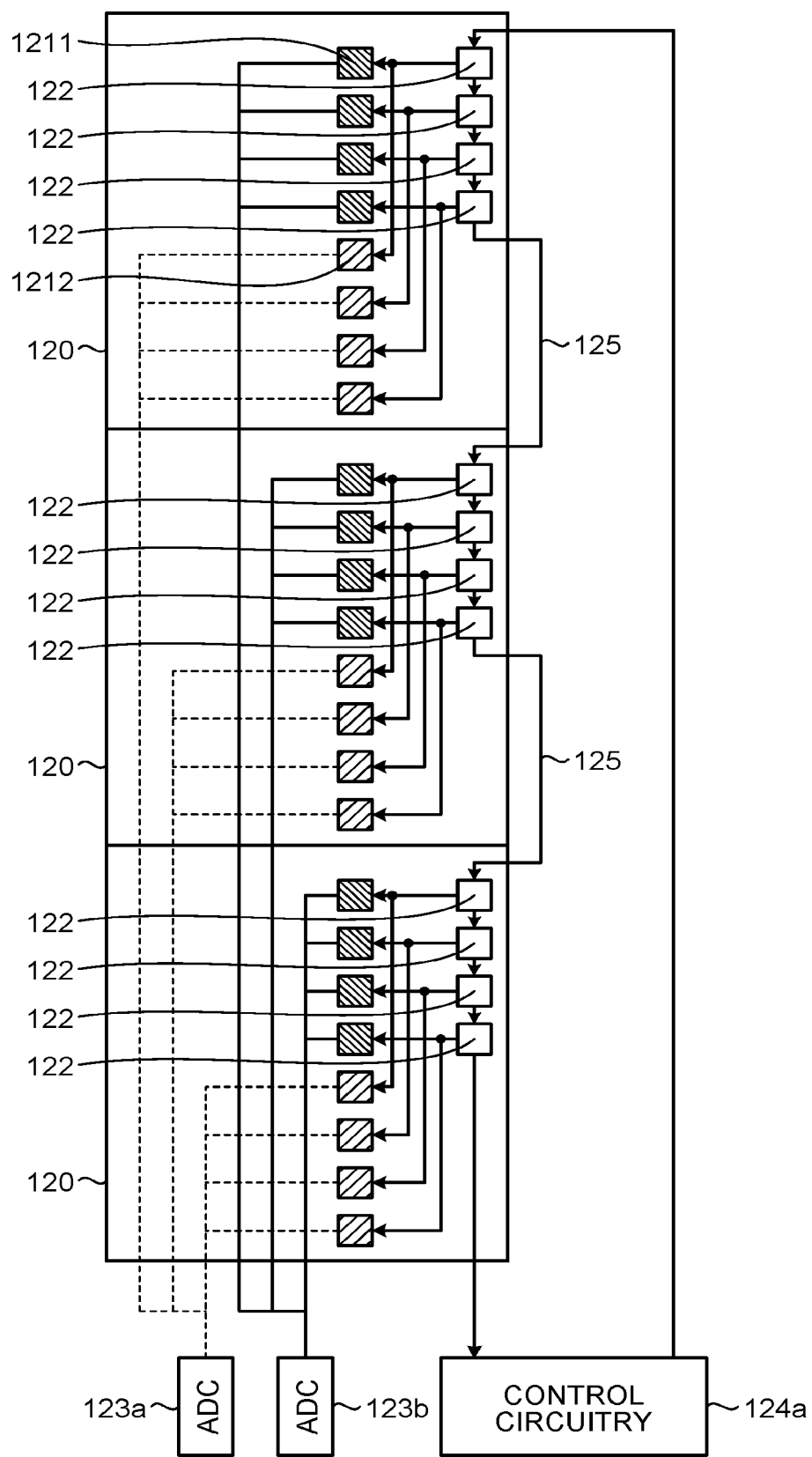
FIG. 8 is a diagram that illustrates an example of the circuitry configuration of the X-ray detector according to a second embodiment.

FIG. 8 is a diagram that illustrates an example of the circuitry configuration of the X-ray detector 12 according to the second embodiment. Although FIG. 8 illustrates the circuitry configuration of the three modules 120 arranged in the row direction, the eight modules 120 are actually arranged in the row direction as illustrated in FIG. 2.

As illustrated in FIG. 8, the X-ray detector 12 according to the second embodiment includes the modules 120, the ADC 123a, the ADC 123b, a control circuitry 124a, and a control line 125. The control line 125 is an example of the control line. Hereinafter, the part having the same configuration as that described in the first embodiment is denoted by the same reference numeral as that in FIG. 3, and its description is omitted.

The control line 125 is mounted on, for example, the board provided after the detecting element 121 to connect the modules 120 and relate the reading timings of the detecting elements 121 included in each of the modules 120. For example, as illustrated in FIG. 8, the control line 125 connects the switches 122 in the modules 120 to transmit an SP signal between the modules 120.

The control circuitry 124a is mounted on the board provided after the detecting element 121 or the DAS 18 to transmit an SP signal to the switch 122 so as to control the reading timing in the X-ray detector 12.

In the X-ray detector 12 illustrated in FIG. 8, the control circuitry 124a transmits an SP signal to the switches 122 in the upper module 120 of FIG. 8 to control the sequential acquisition of electric signals from the four detecting elements 1211 and the four detecting elements 1212. For example, the switch 122 transmits the SP signal by one clock in the direction of the arrows between the switches 122 so as to switch the connection by one clock and execute the sequential acquisition in the reading timing delayed by one clock.

The switch 122 in the upper module 120 transmits the SP signal to the switch 122 in the middle module 120 in the timing by one clock via the control line 125. Thus, the sequential acquisition is executed for the detecting element 1211 and the detecting element 1212 in the middle module 120 in the reading timing delayed by one clock with respect to the upper module 120.

An SP signal is transmitted from the middle module 120 to the lower module 120 via the control line 125 in the same manner so that it is possible to prevent a large gap in the reading timing between the modules 120. The configuration of the X-ray detector in FIG. 8 enables the reading order illustrated in for example FIG. 7A.

Figure 9:
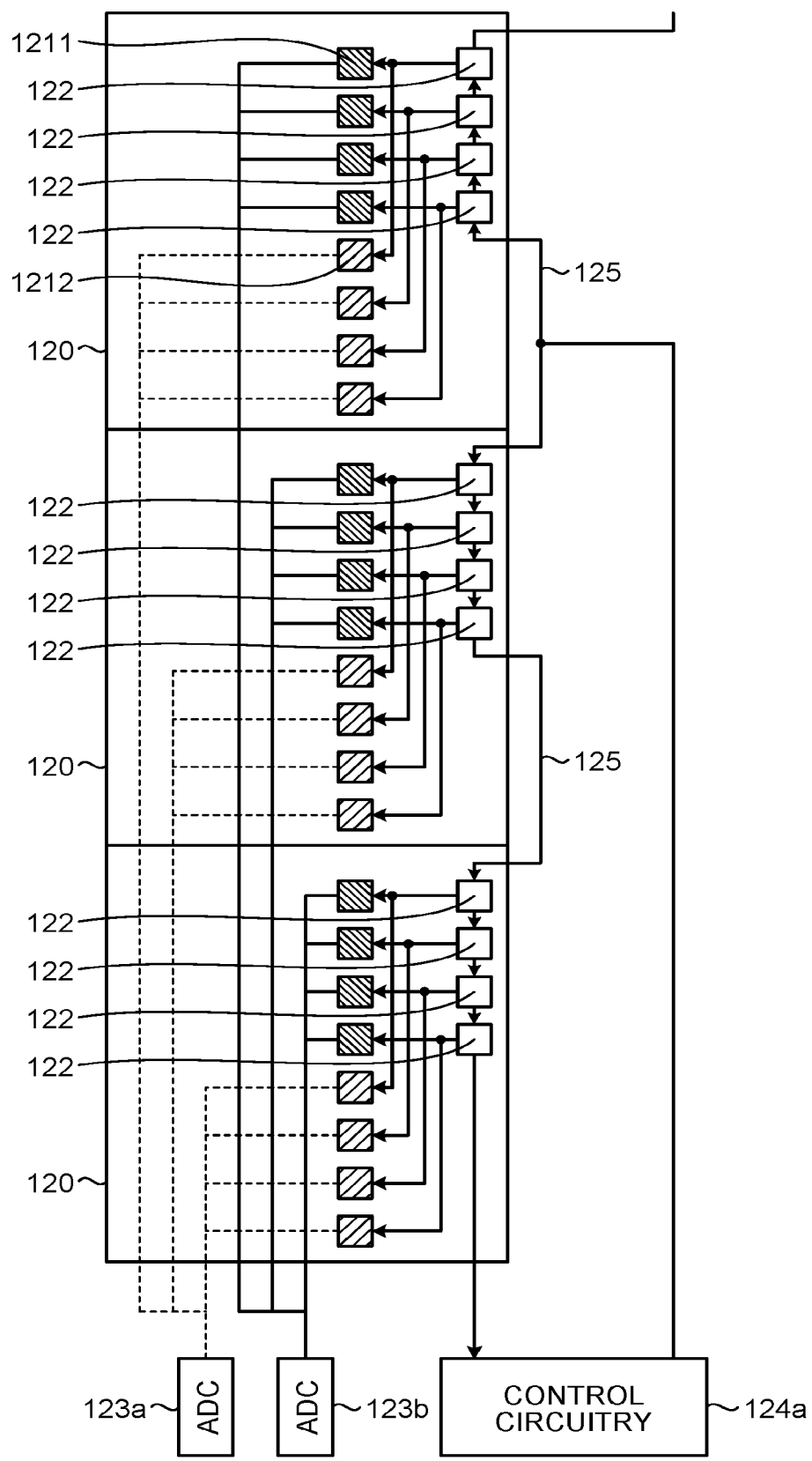
FIG. 9 is a diagram that illustrates an example of the circuitry configuration of the X-ray detector according to the second embodiment.

The reading order illustrated in FIG. 6A is also achieved by using the daisy chain connection between the modules 120. FIG. 9 is a diagram that illustrates an example of the circuitry configuration of the X-ray detector 12 according to the second embodiment. For example, in the X-ray detector 12 that achieves the reading order illustrated in FIG. 6A, an SP signal is input to each of the upper module 120 and the middle module 120, as illustrated in FIG. 9.

The sequential reading is executed in the middle module 120 and the lower module 120 via the control line 125. The sequential reading is executed in the upper module 120 and the further upper module 120 (not illustrated) via the control line 125.

As described above, according to the second embodiment, the modules 120 include the detecting elements 121. The control line 125 connects the modules 120 to relate the reading timings of the detecting elements 121 included in each of the modules 120. The ADC processes signals from the detecting elements 121. Therefore, the X-ray CT apparatus 1 according to the second embodiment may prevent the occurrence of a large gap in the reading timing at the boundary between the modules 120 without controlling the reading on each of the modules 120 with an SP signal and may execute the sequential acquisition appropriately in the X-ray detector 12 where the modules 120 including the detecting elements 121 are arranged in the row direction.

Third Embodiment

In the above-described embodiment, a description is provided for a case where the reading start timing is adjusted for each of the modules 120 and for a case where the modules 120 are daisy-chain connected. In a third embodiment, a description is provided for a case where the reading start timing is adjusted for each of the modules 120 while the modules 120 are daisy-chain connected.

Figure 10:
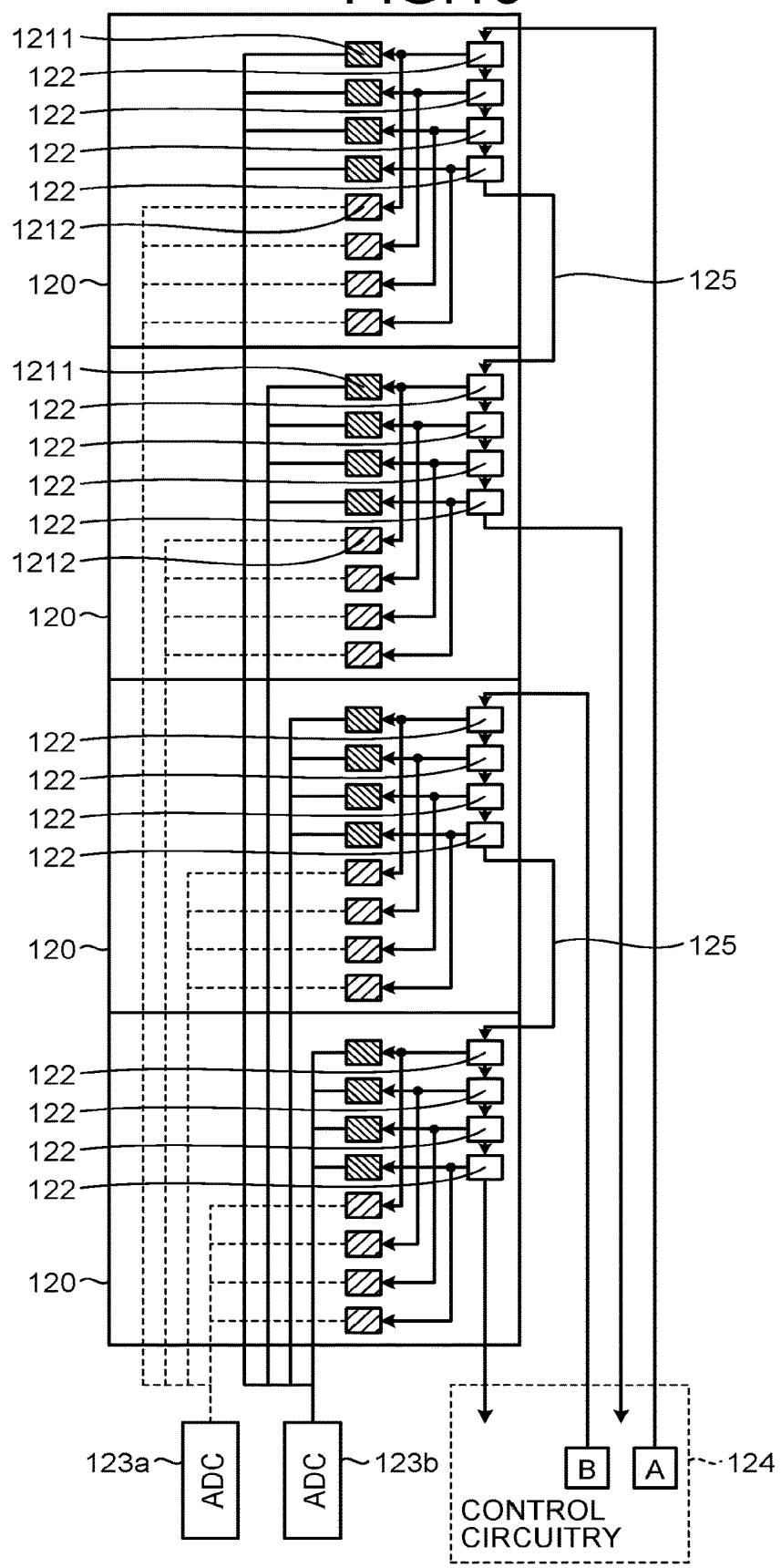
FIG. 10 is a diagram that illustrates an example of the circuitry configuration of the X-ray detector according to a third embodiment.

FIG. 10 is a diagram that illustrates an example of the circuitry configuration of the X-ray detector 12 according to the third embodiment. Although FIG. 10 illustrates the circuitry configuration of the four modules 120 arranged in the row direction, the eight modules 120 are actually arranged in the row direction as illustrated in FIG. 2.

As illustrated in FIG. 10, the X-ray detector 12 according to the third embodiment includes the modules 120, the ADC 123a, the ADC 123b, the control circuitry 124, and the control line 125. Hereinafter, the part having the same configuration as that described in the first embodiment and the second embodiment is denoted by the same reference numeral as that in FIGS. 3 and 8, and its description is omitted.

For example, in the X-ray detector 12 according to the third embodiment, as illustrated in FIG. 10, the upper module 120 and the second module 120 from the top are connected via the control line 125, and the third module 120 from the top and the lower module 120 are connected via the control line 125.

With regard to module groups connected via the control line 125, the control circuitry 124 delays the reading timings of the detecting elements 121 in the module groups. For example, the control circuitry 124 delays the reading timings in the module groups connected via the control line 125 with the SP signal "A" transmitted to the upper module 120 and the SP signal "B" transmitted to the third module 120 from the top.

For example, the control circuitry 124 transmits, to the third module 120 from the top, the SP signal "B" that is controlled such that the reading in the third module 120 from the top is started in the timing delayed by one clock after the final reading based on the SP signal "A". Thus, electric signals are acquired sequentially and seamlessly in order from the detecting elements 1211 and 1212 in the upper module 120 to the detecting elements 1211 and 1212 in the lower module 120. The configuration of the X-ray detector 12 in FIG. 10 achieves the reading order illustrated in for example FIG. 7A.

As described above, according to the third embodiment, the control line 125 connects the modules 120 to relate the reading timings of the detecting elements 121 included in each of the modules 120. For the groups of the modules 120 connected via the control line 125, the control circuitry 124 delays the reading timings of the detecting elements 121 in the groups of the modules 120. Therefore, the X-ray CT apparatus 1 according to the third embodiment may prevent the occurrence of a large gap in the reading timing at the boundary between the modules 120 and may execute the sequential acquisition appropriately in the X-ray detector 12 where the modules 120 including the detecting elements 121 are arranged in the row direction.

Fourth Embodiment

In the case described according to the above embodiment, the reading timing is adjusted in the modules 120 in the row direction. In the case described according to the fourth embodiment, the reading timing is adjusted in the modules in the channel direction. Specifically, according to the fourth embodiment, an ADC is provided for each detecting element group including a plurality of detecting elements arranged in the channel direction. In other words, the number of ADCs provided corresponds to the number of rows. The DAS 18 is connected to each detecting element group via a switch to sequentially acquire signals of X-rays detected by a detecting element group while the X-ray tube 11 generates X-rays.

Figure 11:
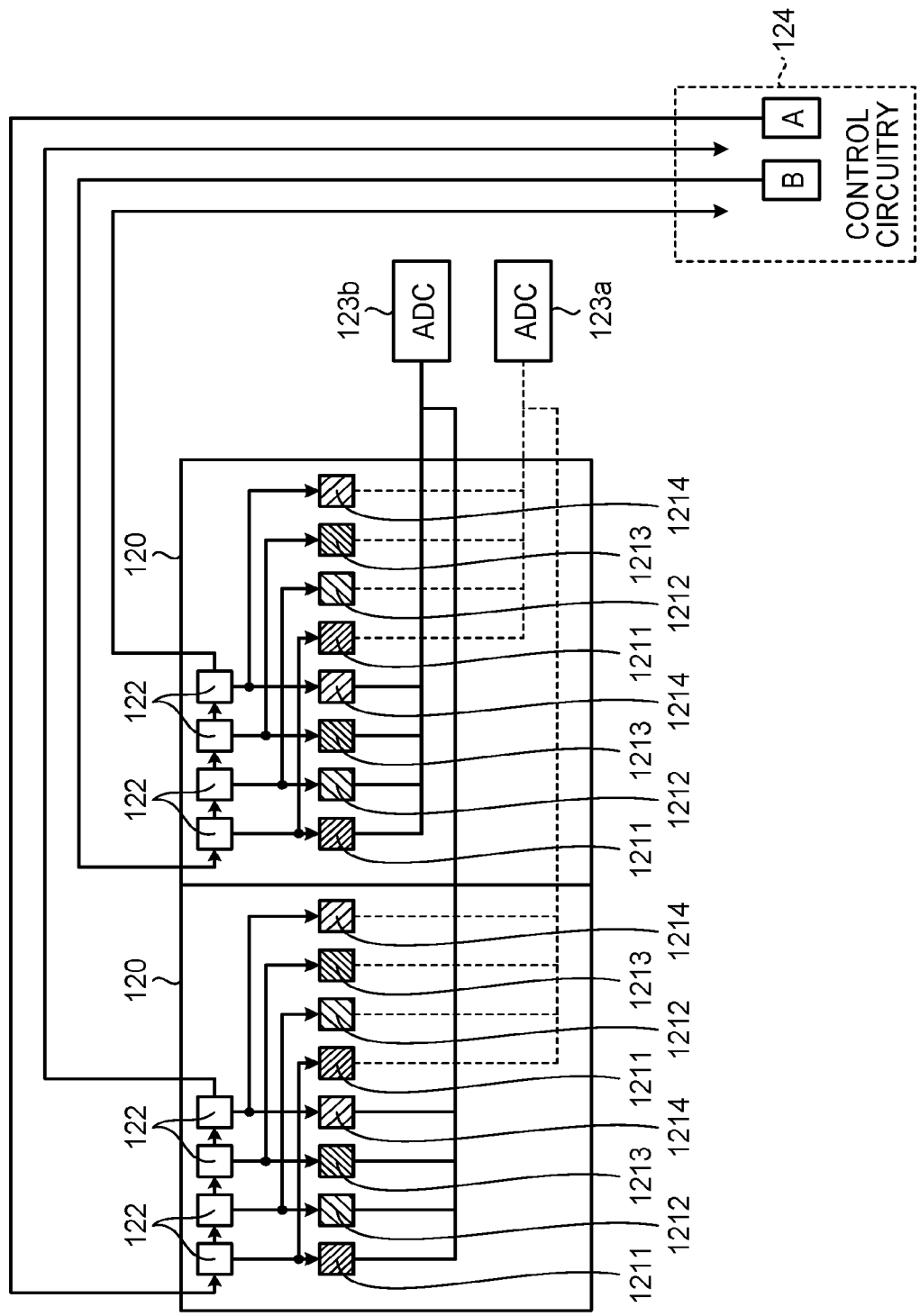
FIG. 11 is a diagram that illustrates an example of the circuitry configuration of the X-ray detector according to a fourth embodiment.

FIG. 11 is a diagram that illustrates an example of the circuitry configuration of the X-ray detector 12 according to the fourth embodiment. Although FIG. 11 illustrates the circuitry configuration of the two modules 120 arranged in the channel direction, the eight modules 120 are further arranged in the row direction in actuality. Specifically, in the X-ray detector 12 according to the fourth embodiment, the modules 120 are arranged in two rows in the channel direction and in eight rows in the row direction. The number of the modules 120 arranged in the channel direction is not limited to two, and the three or more modules 120 may be arranged in the channel direction.

As illustrated in FIG. 11, the X-ray detector 12 according to the fourth embodiment includes the modules 120, the ADC 123a, the ADC 123b, and the control circuitry 124. Hereinafter, the part having the same configuration as that described in the above embodiment is denoted by the same reference numeral as that in FIGS. 3 and 8, and its description is omitted.

Each of the modules 120 includes the detecting elements 121. For example, each of the modules 120 includes the detecting elements 1211 and 1212 and detecting elements 1213 and 1214. The detecting elements 1211 to 1214 in the module 120 illustrated in FIG. 11 represent four detecting elements arranged in the channel direction. Specifically, although the four detecting elements 1211 to 1214 and the four detecting elements 1211 to 1214 are arranged in one row in FIG. 11, the four detecting elements 1211 to 1214 and the four detecting elements 1211 to 1214 are actually arranged in the row direction.

For example, the detecting element 1211 corresponds to the detecting element in the top channel of the module illustrated in FIG. 2 in the row direction that is a horizontal direction. The detecting element 1212 corresponds to the detecting element in the second channel from the top in the row direction that is a horizontal direction in the module illustrated in FIG. 2. The detecting element 1213 corresponds to the detecting element in the third channel from the top in the row direction that is a horizontal direction in the module illustrated in FIG. 2. The detecting element 1214 corresponds to the detecting element in the fourth channel from the top in the row direction that is a horizontal direction in the module illustrated in FIG. 2.

The detecting elements 1211 to 1214 in each row are connected to the switch 122 and the ADC 123b or the switch 122 and the ADC 123a. The detecting elements 1211 to 1214 in each row output electric signals to the ADC 123a or the ADC 123b in accordance with a start pulse signal (SP signal) input from the control circuitry 124 to the switch 122. FIG. 11 illustrates that each of the modules 120 includes, in the row direction, the detecting element groups corresponding to two rows; however, in actuality, detecting element groups in two more rows in the row direction are included, and each detecting element group is connected to a switch and an ADC. The same control content as that described below is performed on each detecting element group.

The control circuitry 124 transmits a unique SP signal to each module to adjust the reading timing of each module. For example, the control circuitry 124 transmits the SP signal "A" to the switch 122 in the left module 120 illustrated in FIG. 11 so as to sequentially acquire electric signals from the detecting elements 1211 to 1214. For example, the switches 122 transmit the SP signal by one clock in the direction of the arrows between the switches 122 to switch the connection by one clock so as to execute the sequential acquisition in the reading timing delayed by one clock.

Similarly, the control circuitry 124 transmits the SP signal "B" to the switch 122 in the right module 120 illustrated in FIG. 11 so as to sequentially acquire electric signals from the detecting elements 1211 to 1214 in the right module 120. The SP signal "B" is a signal controlled such that the reading in the right module 120 is started in the timing delayed by one clock after the last reading based on the SP signal "A". Thus, the reading of the detecting element 1211 in the right module 120 is started one clock after the end of the reading of the detecting element 1214 in the left module 120.

As described above, the X-ray detector 12 according to the fourth embodiment controls the reading timing with an SP signal for each module so as to prevent a gap in the reading timing between modules and execute the sequential acquisition appropriately.

In the example described according to the above embodiment, the reading start timing is adjusted for the modules 120 arranged in the channel direction. The reading timing in the channel direction may be also adjusted by using the daisy chain connection. In such a case, the modules 120 arranged in the channel direction are connected via a control line. For example, the same connection as the daisy chain connection in the row direction as illustrated in FIG. 8 is provided in the channel direction so that the reading timing may be adjusted in the channel direction.

The reading timing in the channel direction may be also adjusted due to the adjustment on the reading start timing of each of the modules 120 and the daisy chain connection between the modules 120. For example, the connection and the control that are the same as the connection in the row direction and the control illustrated in FIG. 10 are applied to the channel direction so that the reading timing in the channel direction may be adjusted.

As described above, according to the fourth embodiment, the modules 120 are arranged in the channel direction. The control circuitry 124 performs the control to change the reading timings of the detecting elements 121 in the modules 120 arranged in the channel direction. Thus, the X-ray CT apparatus 1 according to the fourth embodiment may prevent the occurrence of a large gap in the reading timing at the boundary between the modules 120 and may appropriately execute the sequential acquisition in the X-ray detector 12 where the modules 120 including the detecting elements 121 are arranged in the channel direction.

Fifth Embodiment

In the case described according to the above embodiment, the reading timings are adjusted with regard to the modules 120 in the row direction or the channel direction. In the case described according to a fifth embodiment, the reading timings are adjusted with regard to the modules 120 in the row direction and the channel direction.

Figure 12:
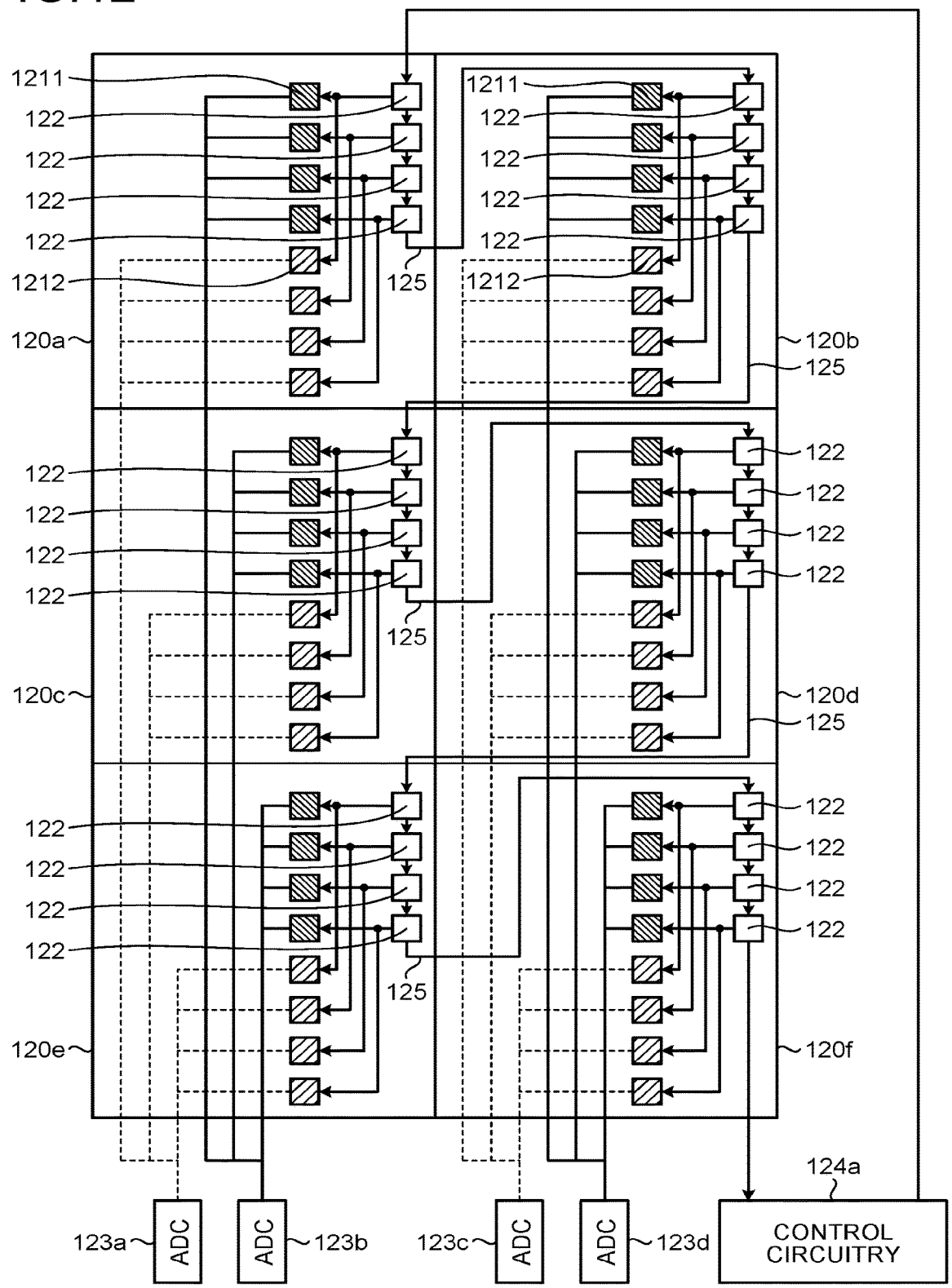
FIG. 12 is a diagram that illustrates an example of the circuitry configuration of the X-ray detector according to a fifth embodiment.

FIG. 12 is a diagram that illustrates an example of the circuitry configuration of the X-ray detector 12 according to the fifth embodiment. Although FIG. 12 illustrates the circuitry configuration of the three modules 120 in the row direction and the two modules 120 in the channel direction, the eight modules 120 are actually arranged in the row direction. The three or more modules 120 may be arranged in the channel direction.

As illustrated in FIG. 12, the X-ray detector 12 according to the fifth embodiment includes modules 120a to 120f, the ADCs 123a and 123b, ADCs 123c and 123d, the control circuitry 124a, and the control line 125. Hereinafter, the part having the same configuration as that described in the above embodiment is denoted by the same reference numeral as that in FIGS. 3 and 8, and its description is omitted.

The ADC 123a receives electric signals sequentially output from the respective detecting elements 1212 included in the module 120a, the module 120c, and the module 120e and converts them into digital signals. The ADC 123b receives electric signals sequentially output from the respective detecting elements 1211 included in the module 120a, the module 120c, and the module 120e and converts them into digital signals. The ADC 123c receives electric signals sequentially output from the respective detecting elements 1212 included in the module 120b, the module 120d, and the module 120f and converts them into digital signals. The ADC 123d receives electric signals sequentially output from the respective detecting elements 1211 included in the module 120b, the module 120d, and the module 120f and converts them into digital signals.

In the X-ray detector 12 illustrated in FIG. 12, the control circuitry 124a transmits an SP signal to the switches 122 in the module 120a to control the sequential acquisition of electric signals from the four detecting elements 1211 and the four detecting elements 1212 in the module 120a. For example, the switch 122 transmits the SP signal by one clock in the direction of the arrows between the switches 122 so as to switch the connection by one clock and execute the sequential acquisition in the reading timing delayed by one clock.

The switch 122 in the module 120a transmits the SP signal to the switch 122 in the module 120b in the timing by one clock via the control line 125. Thus, the sequential acquisition is executed for the detecting element 1211 and the detecting element 1212 in the module 120b in the reading timing delayed by four clocks with respect to the module 120a.

The switch 122 in the module 120b transmits the SP signal to the switch 122 in the module 120c in the timing by one clock via the control line 125. Thus, the sequential acquisition is executed for the detecting element 1211 and the detecting element 1212 in the module 120c in the reading timing delayed by four clocks with respect to the module 120b.

In the same manner, the SP signal is transmitted to the module 120d, the module 120e, and then the module 120f in order. Thus, the sequential acquisition is executed in the modules in the row direction and the modules in the channel direction in the reading timing delayed by four clocks.

In the case described according to the above embodiment, the reading timings in the modules in the row direction and in the channel direction are adjusted by using the daisy chain connection. However, the reading timings in the modules in the row direction and in the channel direction may be also adjusted by adjusting the reading start timings in the modules 120. In such a case, as is the case with for example FIG. 3, the control circuitry 124 is connected to the modules 120a to 120f so as to transmit an SP signal to the switch 122 in each module in the adjusted timing, whereby the reading timings of the modules in the row direction and in the channel direction may be adjusted.

The reading timings of the modules in the row direction and in the channel direction may be also adjusted by adjusting the reading start timing for each of the modules 120 and establishing the daisy chain connection between the modules 120. For example, the module 120a, the module 120c, and the module 120e are daisy-chain connected in the same manner as in FIG. 8. Furthermore, the module 120b, the module 120c, and the module 120e are daisy-chain connected in the same manner as in FIG. 8. The control circuitry 124 transmits an SP signal to the switch 122 in the module 120a and transmits, to the switch 122 in the module 120b, the SP signal controlled such that the reading in the module 120b is started in the timing delayed by one clock.

As described above, according to the fifth embodiment, the control circuitry 124 performs the control to change the reading timings of the detecting elements 121 in the modules 120 arranged in the row direction and the reading timings of the detecting elements 121 in the modules 120 arranged in the channel direction. Thus, the X-ray CT apparatus 1 according to the fifth embodiment may prevent the occurrence of a large gap in the reading timing at the boundary between the modules 120 in the row direction and the channel direction.

Sixth Embodiment

In the case described according to the above embodiment, the ADC is provided for each row or each channel. In the case described according to a sixth embodiment, an ADC is provided for each of the modules 120.

Figure 13A:
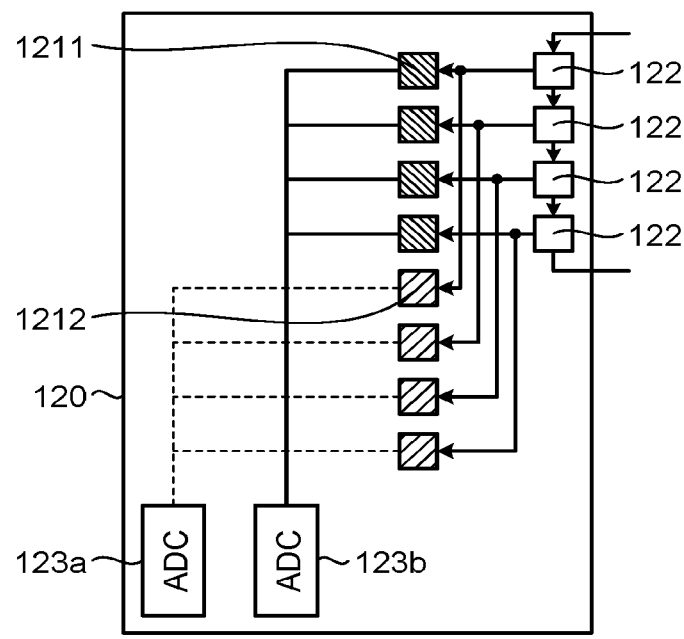
FIG. 13A is a diagram that illustrates an example of the circuitry configuration of the X-ray detector according to a sixth embodiment.
Figure 13B:
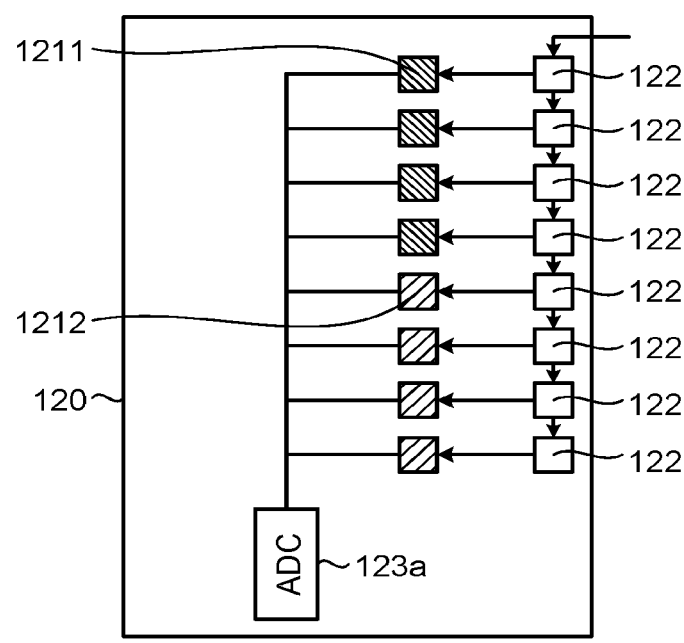
FIG. 13B is a diagram that illustrates an example of the circuitry configuration of the X-ray detector according to the sixth embodiment.

FIGS. 13A and 13B are diagrams that illustrate examples of the circuitry configuration of the X-ray detector 12 according to the sixth embodiment. Although FIGS. 13A and 13B illustrate the circuitry configuration of the single module 120, all the modules 120 included in the X-ray detector 12 have the same configuration in actuality. Hereinafter, the part having the same configuration as that described in the above embodiment is denoted by the same reference numeral as that in FIG. 3, and its description is omitted.

As illustrated in for example FIG. 13A, the X-ray detector 12 according to the sixth embodiment includes the ADC 123a and the ADC 123b for each of the modules 120. The ADC 123a and the ADC 123b may be located at any position as long as they are included in each of the modules 120. Although not illustrated, the ADC 123a and the ADC 123b are connected to the control circuitry 124 so that the timing of signal processing is controlled.

The control circuitry 124 according to the sixth embodiment performs the control to change the timing of a signal output from the detecting element 121 and the timing of signal processing in the ADC. That is, according to the sixth embodiment, as the ADC is provided for each of the modules 120, the control circuitry 124 controls the timing of switching of the switch 122 and the timing of conversion of the ADC to adjust the reading timing. For example, the control circuitry 124 transmits control signals to the ADC 123a and the ADC 123b so as to convert an electric signal output from each detecting element in accordance with a transmitted SP signal into a digital signal.

The X-ray detector 12 according to the sixth embodiment may include the single ADC 123a for the detecting elements 1211 and the detecting elements 1212 as illustrated in for example FIG. 13B. In such a case, the module 120 includes the eight switches 122 corresponding to the eight detecting elements.

As described above, according to the sixth embodiment, the ADC is provided for each module. The control circuitry 124 performs the control to change the timing of a signal output from the detecting element 121 and the timing of signal processing in the ADC. Thus, the X-ray CT apparatus 1 according to the sixth embodiment enables the appropriate sequential acquisition even in a case where the ADC is provided for each of the modules 120.

Other Embodiments

Although the first embodiment to the sixth embodiment are described above, various different embodiments may be implemented other than the above-described first to sixth embodiments.

In the case described according to the above embodiment, the X-ray detector 12 includes the 32 detecting elements 121 in the row direction. However, the embodiment is not limited thereto, and the X-ray detector 12 may include the detecting elements 121 in any number of rows as long as the detecting elements 121 in the number of rows may be tiled in the row direction.

In the case described according to the above embodiment, the module 120 has four rows in the channel direction and four rows in the row direction. However, the embodiment is not limited thereto, and the module 120 may include any number of rows.

The term "processor" used in the above description means, for example, a CPU, a GPU (graphics processing unit), or a circuit, such as an application specific integrated circuit (ASIC), a programmable logic device (e.g., a simple programmable logic device (SPLD), a complex programmable logic device (CPLD), or a field programmable gate array (FPGA)). The processor reads a program stored in the memory 41 and executes it to implement the function.

In the description with reference to FIG. 1, the single memory 41 stores the program corresponding to each processing function. However, the embodiment is not limited thereto. For example, a configuration may be such that the multiple memories 41 are separately provided and the processing circuitry 44 reads the corresponding program from the individual memory 41. A configuration may be such that, instead of storing the program in the memory 41, the program is directly installed in a circuitry of the processor. In this case, the processor reads and executes the program installed in the circuitry to perform the function.

The processing circuitry 44 may use a processor of an external device connected via a network to perform a function. For example, the processing circuitry 44 reads and executes the program corresponding to each function from the memory 41 and uses an external workstation or cloud connected to the X-ray CT apparatus 1 via a network NW as computational resources to perform each of the functions illustrated in FIG. 1.

Components of each device according to the above-described embodiment are conceptual in terms of functionality and do not necessarily need to be physically configured as illustrated in the drawings. Specifically, specific forms of separation and combination of each device are not limited to those depicted in the drawings, and a configuration may be such that all or some of them are functionally or physically separated or combined in an arbitrary unit depending on various types of loads or usage. All or any of various processing functions performed by each device may be implemented by a CPU or a program analyzed and executed by the CPU or may be implemented by wired logic hardware.

According to at least one of the above-described embodiments, an X-ray detector using a module including a plurality of detecting elements may execute the sequential acquisition appropriately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An X-ray detector, comprising:
a plurality of detection arrays, each of the plurality of detection arrays including (1) a plurality of detecting elements, and (2) a port configured to receive a start command to control reading from "m" detecting elements of the plurality of detecting elements, wherein "m" is greater than 1;

processing circuitry configured to perform sequential reading in a predetermined reading direction from the "m" detecting elements for each of the detection arrays by sending start commands to the respective ports; and plural analog-to-digital converters (ADC) configured to process signals from the plurality of detecting elements, wherein each ADC of the plural ADCs is connected to a group of "m" detecting elements of the plurality of detecting elements that are read in response to receiving the respective start command, wherein the processing circuitry is further configured to send a start command with a delayed read start timing to a port of a second detection array located adjacent to, and on a downstream side in the predetermined reading direction of, a first detection array, the first and second detection arrays having a same reading direction, the delayed read start timing being delayed with respect to a read start time of the first detection array according to a number of the "m" detecting elements.

2. The X-ray detector according to claim 1, further comprising a control line configured to connect first and second m-bit shift registers of first and second detection arrays of the plurality of detection arrays and relate reading timings of a plurality of detecting elements included in each of the first and second detection arrays.

3. The X-ray detector according to claim 1, wherein
the detection arrays are arranged in a row direction or a channel direction, and
the processing circuitry is further configured to perform control to change reading timings between the plurality of detection arrays arranged in the row direction or the channel direction.

4. The X-ray detector according to claim 1, wherein
the detection arrays are arranged in a row direction and a channel direction, and
the processing circuitry is further configured to perform control to change reading timings between the plurality of detection arrays arranged in the row direction and reading timings between the plurality of detection arrays arranged in the channel direction.

5. The X-ray detector according to claim 1, wherein the plural ADCs are controllably connected to each of the plurality of detection arrays.

6. The X-ray detector according to claim 5, wherein the processing circuitry is further configured to control timing of when respective detecting elements of the plurality of detecting elements are connected to a respective ADC of the plural ADCs.

7. An X-ray CT apparatus comprising the X-ray detector according to claim 1.

8. The X-ray detector according to claim 1,
wherein the plurality of detections arrays is "q" detection arrays,
wherein the plurality of detection elements in the "q" detection arrays comprise an "m"×"n" array of detection elements in each of the "q" detection arrays,
wherein "m" detection elements are grouped in a first direction, and "n" groups of "m" detection elements are grouped in a second direction orthogonal to the first direction, and
wherein the plural ADCs comprise "n" ADCs with one of the "n" ADCs connected to a corresponding one of the "n" groups of "m" detection elements.

9. The X-ray detector according to claim 8, wherein "q" m-bit switches sequentially couple, in consecutive clock cycles, first and second adjacent detector elements of the "m" detector elements to the corresponding one of the "n" ADCs.

10. An X-ray detector, comprising:
a plurality of detection arrays, each of the plurality of detection arrays including (1) a plurality of detecting elements, and (2) a m-bit shift register for receiving a start command to control reading from "m" detecting elements of the plurality of detecting elements, wherein "m" is greater than 1;
a control line configured to connect first and second m-bit shift registers of respective first and second detection arrays of the plurality of detection arrays, the first and second detection arrays being adjacent to each other and having a same reading direction;
processing circuitry configured to perform sequential reading in which reading from "m" detecting elements of the first detection array and reading from "m" detecting elements of the second detection array are performed sequentially along the reading direction by sending a start command to the first m-bit shift register of the first detection array, the first detection array being located on a upstream side in the reading direction, which extends from the first detection array to the second detection array; and
plural analog-to-digital converters (ADC) configured to process signals from the plurality of detecting elements, wherein each ADC of the plural ADCs is connected to a group of "m" detecting elements of the plurality of detecting elements that are read in response to receiving the respective start command,
wherein the processing circuitry is further configured to send start commands with a same read start timing to third and fourth m-bit shift registers of respective third and fourth detection arrays of the plurality of detection arrays respectively, the third and fourth detection arrays being adjacent to one another and having opposite reading directions.

11. The X-ray detector according to claim 10, wherein
the plurality of detection arrays are arranged in a row direction or a channel direction, and
the control line is configured to connect the plurality of detection arrays arranged in the row direction or the channel direction.

12. The X-ray detector according to claim 10, wherein
the plurality of detection arrays are arranged in a row direction and a channel direction, and
the control line is configured to connect the detection arrays arranged in the row direction and the detection arrays arranged in the channel direction.

13. The X-ray detector according to claim 10, wherein the plural ADCs are controllably connected to each of the plurality of detection arrays.

14. The X-ray detector according to claim 13, wherein the processing circuitry is further configured to control timings of when respective detecting elements of the plurality of detecting elements are connected to a respective ADC of the plural ADCs.

15. An X-ray CT apparatus comprising the X-ray detector according to claim 10.

16. The X-ray detector according to claim 10,
wherein the plurality of detections arrays is "q" detection arrays,
wherein the plurality of detection elements in the "q" detection arrays comprise an "m"×"n" array of detection elements in each of the "q" detection arrays, wherein "m" detection elements are grouped in a first direction, and "n" groups of "m" detection elements are grouped in a second direction orthogonal to the first direction, and wherein the plural ADCs comprise "n" ADCs with one of the "n" ADCs connected to a corresponding one of the "n" groups of "m" detection elements.

\* \* \* \* \*